(12) United States Patent
Matsumoto et al.

(10) Patent No.: US 6,743,923 B2
(45) Date of Patent: Jun. 1, 2004

(54) ANTIRHEUMATIC AGENT

(75) Inventors: Saichi Matsumoto, Ikeda (JP); Hirokuni Jyoyama, Nara (JP); Shinji Kakudo, Kawanishi (JP); Kohji Hanasaki, Kyoto (JP); Kenzo Koizumi, Sakai (JP); Tsuneaki Sakata, Toyonaka (JP); Ryuji Suzuki, Ikoma-gun (JP)

(73) Assignee: Shionogi & Co., Ltd., Osaka (JP)

( * ) Notice: Subject to any disclaimer, the term of this patent is extended or adjusted under 35 U.S.C. 154(b) by 27 days.

(21) Appl. No.: 10/309,256

(22) Filed: Dec. 4, 2002

(65) Prior Publication Data

US 2003/0125364 A1 Jul. 3, 2003

Related U.S. Application Data

(62) Division of application No. 09/530,082, filed as application No. PCT/JP98/04774 on Oct. 22, 1998, now Pat. No. 6,525,081.

(30) Foreign Application Priority Data

Oct. 24, 1997 (JP) .............................. 9-292517

(51) Int. Cl.$^7$ ............................ C07D 275/02
(52) U.S. Cl. ..................................... 548/214
(58) Field of Search ........................ 548/214

(56) References Cited

U.S. PATENT DOCUMENTS 5,418,230 A 5/1995 Matsumoto et al.
5,618,835 A 4/1997 Wu et al.

FOREIGN PATENT DOCUMENTS

| EP | 0595546 | 5/1994 |
|----|---------|--------|
| JP | 6-211819 | 8/1994 |
| WO | 98/52563 | 11/1998 |
| WO | 99/21554 | 6/1999 |

OTHER PUBLICATIONS

F. Breedveld, "Tenidap: A Novel Cytokine–modulating Antirheumatic Drug For the Treatment of Rheumatoid Arthritis", Scandinavian Journal of Rheumatology 1994; 23 (Suppl 100): pp. 31–44.

*Primary Examiner*—Robert Gerstl
(74) *Attorney, Agent, or Firm*—Wenderoth, Lind & Ponack, L.L.P.

(57) ABSTRACT

A novel antirheumatic agent comprising as an active ingredient a compound of formula I:

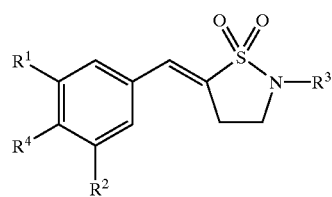

or a pharmaceutically acceptable salt or hydrate thereof.

5 Claims, 7 Drawing Sheets

ANTIRHEUMATIC AGENT

This application is a divisional application of Ser. No. 09/530,082 filed Apr. 24, 2000, now U.S. Pat. No. 6,525,081, which is a 371 National Phase Application of PCT/JP98/04774 filed Oct. 22, 1998.

TECHNICAL FIELD

The present invention relates to novel benzylidene derivatives, and an antirheumatic agent, an osteoclast formation inhibiting agent, a nitrogen monoxide production inhibiting agent, and a transcription factor NFκB suppressing agent comprising said benzylidene derivative as an active ingredient. The present invention further relates to a method for the prevention and/or treatment of rheumatic diseases, a method for the inhibition of osteoclast formation, a method for the inhibition of nitrogen monoxide production, and a method for the suppression of transcription factor NFκB.

BACKGROUND ART

Rheumatic disease is a systemic inflammatory disease involving a functional abnormality accompanied by swellings and pains in arthrosis as the primary symptom. The number of the patients in Japan is estimated as more than about 600 thousands (morbidity: about 0.5% of the Japanese population), and many of these patients are females of middle to advanced age. Although the development of this disease has not yet been well elucidated, it is believed to be a trigger for this disease that an immunological abnormality occurs for some reason, the autoimmune response is accelerated, and an activated macrophage, neutrophil, T-cell and the like are infiltrated to inflammatory focus. Then, these cells receive an inflammatory stimulus to produce various inflammatory mediators such as IL-1, IL-6, THF-α, nitrogen monoxide (NO) and prostaglandin $E_2$ ($PGE_2$). The mediators then induce a cell adhesion factor, collagenase, protease and the like, which cause swelling and pain and accelerate the destruction of articular cartilage and bone.

According to the recent findings, activation of NFκB due to inflammatory stimulation induces cyclooxygenase-2 (COX-2) and inductive nitrogen monoxide synthase (i-NOS), and also accelerates an expression of cytokines. Cytokines and NO produced in the inflammatory focus activate NFκB. As a result, it is believed that the production of inflammatory mediators is enhanced in the inflammatory focus and the chronic inflammation pathology accompanied by the tissue destruction is thus developed. NO is also associated with the activation of COX-2 and accelerates production of $PGE_2$.

Certain benzylidene compounds exhibit an anti-inflammatory effect, and therefore, they are currently used in the treatment of rheumatic diseases as a nonsteroidal anti-inflammatory drug (NSAID), for the purpose of suppressing pains and swellings. However, the use of such nonsteroidal anti-inflammatory drug is a mere symptomatic therapy for the suppression of pains and swellings due to rheumatic diseases and is not curable for the disease itself.

On the other hand, antirheumatic agents (disease-modifying antirheumatic drug) inhibit the progression of rheumatic pathology and they are used in a radical therapy for the disease. The compounds of the present invention have been found to inhibit articular bone destruction, a rheumatic pathology, in a rheumatic model animal (NZB/KN) to which a nonsteroidal anti-inflammatory drug is not effective. Thus, the compounds have been found to be effective in a radical therapy of rheumatic diseases via a different mechanism from that of anti-inflammatory agents.

Combination use of a disease-modifying antirheumatic drug (DMARD) such as immunosuppressants or immuno-modulators and a nonsteroidal anti-inflammatory drug (NSAID) is often conducted in the treatment of chronic arthritis such as rheumatoid arthritis. However, these drug have drawbacks in that the former may often cause serious side effects such as blood disorder, and the latter may cause gastrointestinal disorder due to prolonged administration. Accordingly, a drug which possesses the DMARD and NSAID effects but less side effects would be very useful as a therapeutic agent for rheumatoid arthritis.

SUMMARY OF THE INVENTION

The present inventors have found that particular benzylidene derivatives, i.e. the compounds of formula I:

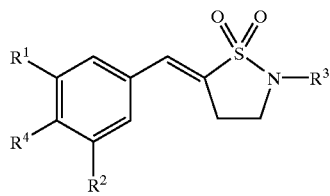

wherein
  $R^1$ is hydrogen, lower alkyl, lower alkoxy, hydroxy lower alkyl, or carboxy lower alkyl and $R^4$ is hydroxy; or
  $R^1$ and $R^4$ taken together form —$CR^5R^6$—$(CH_2)_m$—O— or —$CR^5R^6$—$(CH_2)_p$CH(OH)—O—
    wherein m is an integer of 1 to 3;
    p is an integer of 0 to 2; and
    R5 and R6 are each independently hydrogen, lower alkyl, lower alkoxy, or hydroxy lower alkyl;
  $R^2$ is hydrogen, lower alkyl, lower alkoxy, hydroxy lower alkyl, or carboxy lower alkyl; and
  $R^3$ is hydrogen, lower alkyl, cycloalkyl, lower alkoxy, arylalkyloxy, heteroarylalkyloxy, lower alkylcarbonyl, arylcarbonyl, substituted or unsubstituted carbamoyl or the group represented by the formula:

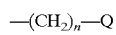

wherein Q is hydroxy, substituted or unsubstituted amino, aryl, heteroaryl, hydroxycarbonyl or lower alkyloxycarbonyl; and
  n is an integer of 0 to 3
exhibit not only anti-inflammatory effect but also antirheumatic effect. The present invention has been accomplished on the basis of the above finding.

The present inventors also have found that the above compounds inhibit enhanced formation of osteoclast caused by $PGE_2$.

Also, the above compounds have been found to suppress an inducible nitrogen monoxide synthase (i-NOS) to inhibit NO production.

Further, the above compounds have been found to posses suppressive activity on a transcription factor NFκB.

Accordingly, the present invention provides novel uses of such derivatives as an antirheumatic agent, an osteoclast formation inhibiting agent, a nitrogen monoxide production inhibiting agent, and a transcription factor NFκB suppressing agent.

Thus, the present invention provides an antirheumatic agent comprising a compound of formula I or pharmaceutically acceptable salt or hydrate thereof as an active ingredient.

The present invention also provides an osteoclast formation inhibiting agent comprising a compound of formula I or pharmaceutically acceptable salt or hydrate thereof as an active ingredient.

The present invention further provides a nitrogen monoxide production inhibiting agent comprising a compound of formula I or pharmaceutically acceptable salt or hydrate thereof as an active ingredient.

The present invention yet further provides a transcription factor NFκB suppressing agent comprising a compound of formula I or pharmaceutically acceptable salt or hydrate thereof as an active ingredient.

The compounds of the formula I wherein $R^1$ and $R^2$ are both t-butyl, more preferably $R^1$ and $R^2$ are both t-butyl and $R^4$ is hydroxy, more preferably $R^1$ and $R^2$ are both t-butyl, $R^3$ is lower alkyl and $R^4$ is hydroxy, much more preferably $R^1$ and $R^2$ are both t-butyl, $R^3$ is ethyl and $R^4$ is hydroxy, are preferred antirheumatic agents, osteoclast formation inhibiting agents, nitrogen monoxide production inhibiting agents and transcription factor NFκB suppressing agents.

The present invention further provides use of the compounds of formula I for the manufacture of anti-rheumatic agent.

Also, the present invention provides use of the compounds of formula I for the manufacture of osteoclast formation inhibiting agent.

Further, the present invention provides use of the compounds of formula I for the manufacture of nitrogen monoxide production inhibiting agent.

Yet further, the present invention provides use of the compounds of formula I for the manufacture of transcription factor NFκB suppressing agent.

The present invention further provides a method for the prevention and/or treatment of rheumatoid arthritis which comprises administering an effective amount of a compound of formula I to mammals in need thereof.

Also, the present invention provides a method for the inhibition of osteoclast formation which comprises administering an effective amount of a compound of formula I to mammals in need thereof.

Further, the present invention provides a method for the inhibition of nitrogen monoxide production which comprises administering an effective amount of a compound of formula I to mammals in need thereof.

Yet further, the present invention provides a method for the suppression of transcription factor NFκB which comprises administering an effective amount of a compound of formula I to mammals in need thereof.

Among the compounds represented by the above formula I, some compounds have been disclosed as inhibiting agent against $PGE_2$ production in Japanese Patent Publication No. 211819/1994 (published on Aug. 2, 1994).

The present invention further provides novel compounds of formula I':

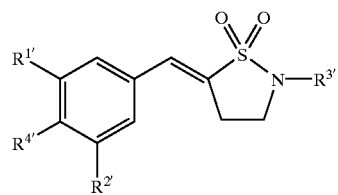

wherein
$R^{1'}$ is hydroxy lower alkyl or carboxy lower alkyl and $R^{4'}$ is hydroxy; or $R^{1'}$ and $R^{4'}$ taken together form —$CR^5R^6$—$(CH_2)_m$—O— or —$CR^5R^6$—$(CH_2)_p$CH(OH)—O—
wherein m is an integer of 1 to 3;
p is an integer of 0 to 2; and
R5 and R6 are each independently hydrogen, lower alkyl, lower alkoxy, or hydroxy lower alkyl;

$R^{2'}$ is hydrogen, lower alkyl, lower alkoxy, hydroxy lower alkyl, or carboxy lower alkyl; and $R^{3'}$ is hydrogen, lower alkyl, cycloalkyl, lower alkoxy, arylalkyloxy, heteroarylalkyloxy, lower alkylcarbonyl, arylcarbonyl, substituted or unsubstituted carbamoyl or the group represented by the formula:

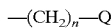
—$(CH_2)_n$—Q wherein Q is hydroxy, substituted or unsubstituted amino, aryl, heteroaryl, hydroxycarbonyl or lower alkyloxycarbonyl; and
n is an integer of 0 to 3
or pharmaceutically acceptable salt or hydrate thereof.

DETAILED DESCRIPTION

Figure 1:
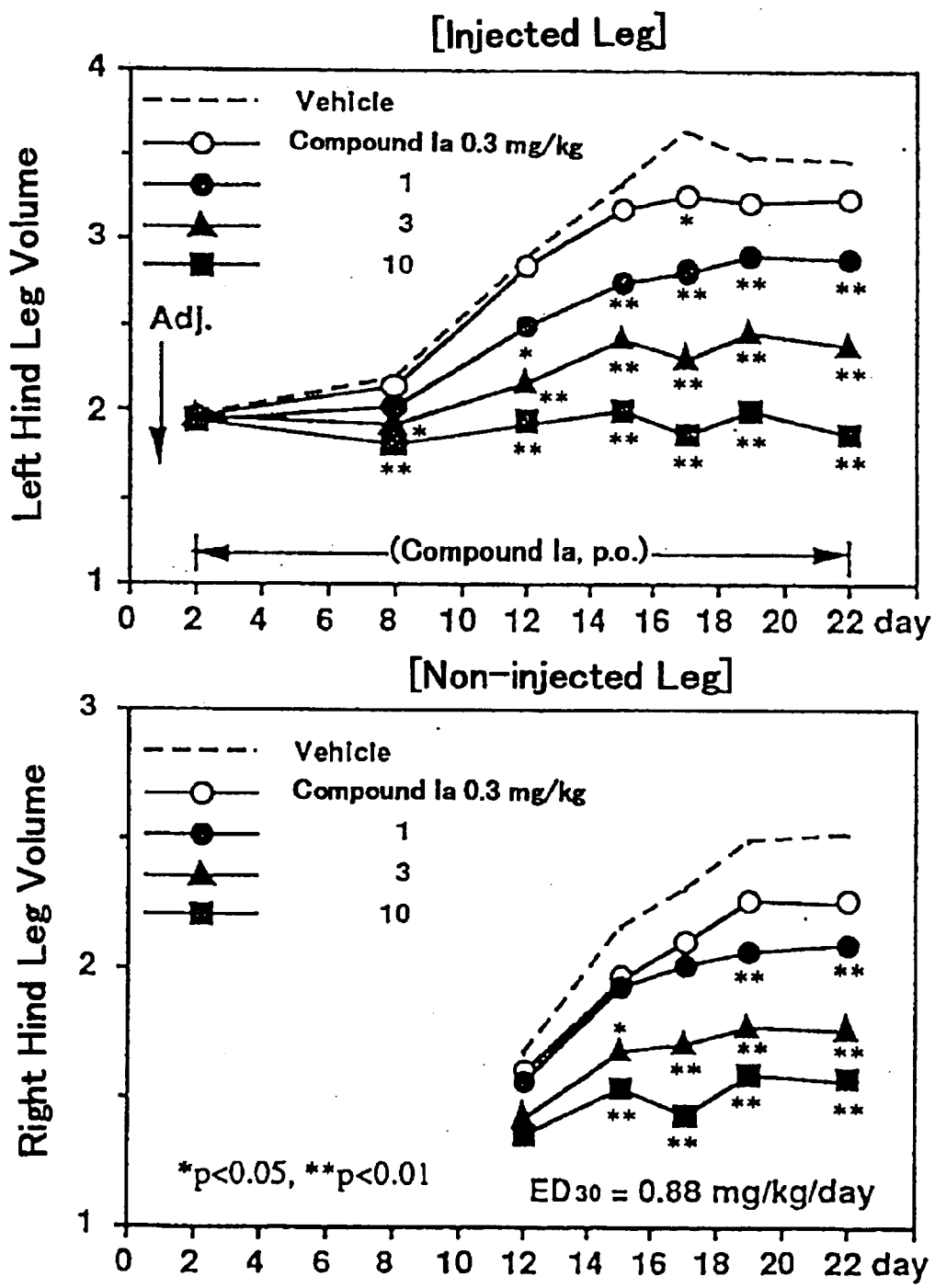
FIG. 1 is a graph showing the inhibitory effect of the compound of the invention against adjuvant articular swelling. Values in the graph are mean of the eight independent experiments, and significance test was performed according to Dunnett's t-test (*p<0.05, **p<0.01: vs. vehicle group).

As is apparent from the above formula, the compounds of the invention of formula I can exist in the stereostructures of (E)-type. Accordingly, unless otherwise noted, the compound I described in this specification should be construed to include (E)-isomer.

For purposes of the present invention, as disclosed and claimed herein, the following terms are defined as below.

The term "lower alkyl" means straight or branched $C_1$–$C_8$ alkyl and examples thereof include methyl, ethyl, n-propyl, i-propyl n-butyl, i-butyl, s-butyl, t-butyl, n-pentyl, i-pentyl, neopentyl, s-pentyl, t-pentyl, n-hexyl, neohexyl, i-hexyl, s-hexyl, t-hexyl, heptyl and octyl. Among them, a straight or branched $C_1$–$C_4$ alkyl is preferred. The most preferred one is methyl or ethyl.

The term "lower alkoxy" means straight or branched $C_1$–$C_6$ alkyloxy and examples thereof include methoxy, ethoxy, n-propoxy, i-propoxy, n-butoxy, i-butoxy, s-butoxy, t-butoxy, n-pentyloxy, i-pentyloxy, neopentyloxy, s-pentyloxy, t-pentyloxy, n-hexyloxy, neohexyloxy, i-hexyloxy, s-hexyloxy and t-hexyloxy and the like. Among them, a $C_1$–$C_3$ alkoxy group is preferred. The most preferred one is methoxy.

The term "hydroxy lower alkyl" means a group formed by substituting the lower alkyl group defined above with hydroxy group(s). Specific examples thereof include hydroxymethyl, hydroxyethyl, hydroxypropyl, hydroxybutyl, 1,1-dimethyl-2-hydroxyethyl and the like.

The term "carboxy lower alkyl" means a group formed by substituting the lower alkyl group defined above with carboxy group(s). Examples thereof include carboxymethyl, carboxyethyl, carboxypropyl, carboxybutyl, 1,1-dimethyl-2-carboxyethyl and the like.

The term "cycloalkyl" means $C_3$–$C_7$ cycloalkyl and examples thereof include cyclopropyl, cyclobutyl, cyclopentyl, cyclohexyl, cycloheptyl and the like. Among them, $C_3$–$C_5$ cycloalkyl is preferred.

The term "aryl" means unsubstituted or substituted phenyl or naphthyl and may be substituted by one or more substituents including halogen, lower alkoxy, lower alkyl, nitro and the like. Examples of aryl include phenyl, 4-chlorophenyl, 4-methoxyphenyl, 4-nitrophenyl, 3,4-dichlorophenyl, 3,4-dimethoxyphenyl, 3,4-dinitrophenyl, 1-naphtyl, 2-naphtyl and the like.

The term "arylalkyloxy" means a group formed by substituting a lower alkoxy group with an aryl group(s) as defined above and examples thereof include benzyloxy, 4-chlorobenzyloxy, 4-methoxybenzyloxy, 3,4-dichlorobenzyloxy, 3,4-dimethoxybenzyloxy, 4-nitrobenzyloxy, 2-phenylethyloxy, 2-(4-chlorophenyl) ethyloxy, 2-(4-methoxyphenyl)ethyloxy, 1-naphtylmethyloxy, 2-naphtylmethyloxy and the like. Among them, benzyloxy is preferred.

The term "heteroaryl" means a group containing 1–4 hetero atoms and examples thereof include pyridyl, thiazolyl, isothiazolyl, oxazolyl, isoxazolyl, imidazolyl, triazolyl and tetrazolyl. For purposes of the present invention, pyridyl, thiazolyl, oxazolyl and imidazolyl are preferred and pyridyl is most preferred.

The term "heteroarylalkyloxy" means a group formed by substituting an alkoxy group with a heteroaryl group(s) as defined above and examples thereof include 2-pyridylmethyloxy, 3-pyridylmethyloxy, 4-pyridylmethyloxy, 2-imidazolylmethyloxy, 4-imidazolylmethyloxy, 2-thiazolylmethyloxy, 4-thiazolylmethyloxy and the like.

Examples of "lower alkylcarbonyl" include acetyl, propionyl, butyryl, valeroyl, hexanoyl, heptanoyl and octanoyl.

Examples of "arylcarbonyl" include benzoyl, 4-chlorobenzoyl, 4-methoxybenzoyl, 4-nitrobenzoyl, 3,4-dichlorobenzoyl, 3,4-dimethoxybenzoyl, 3,4-dinitrobenzoyl, 1-naphthoyl, 2-naphthoyl and the like.

For the term "substituted or unsubstituted carbamoyl", examples of the substituent therefor include lower alkyl, lower alkoxy, hydroxy, cycloalkyl, arylalkyl, alkoxyalkyl, alkylcarbonyl, arylcarbonyl, cycloalkyloxy and arylalkyloxy, and one or more of these substituents may be substituted at the nitrogen atom. Among them, lower alkyl, lower alkoxy and hydroxy are preferred. Examples of substituted carbamoyl include N-methylcarbamoyl, N,N-dimethylcarbamoyl, N-hydroxycarbamoyl, N-methyl-N-hydroxycarbamoyl, N-methoxycarbamoyl, N-methoxy-N-methylcarbamoyl, N-ethylcarbamoyl, N,N-diethylcarbamoyl, N-ethyl-N-hydroxycarbamoyl, N-propylcarbamoyl, N,N-dipropylcarbamoyl and N-propyl-N-hydroxycarbamoyl.

Examples of "halogen" include fluorine, chlorine, bromine and iodine.

Examples of "lower alkyloxycarbonyl" include methoxycarbonyl, ethoxycarbonyl, propoxycarbonyl, isopropoxycarbonyl, butoxycarbonyl, isobutoxycarbonyl, tert-butoxycarbonyl and the like.

The term "substituted amino" means mono- or di-substituted amino, and examples of substituent include lower alkyl and arylalkyl as defined above.

The term "pharmaceutically acceptable salt or hydrate" refers to salts or hydrates of the compounds represented by the formula I which are non-toxic to a living thing. Typical pharmaceutically acceptable salts include inorganic or organic salts formed by the reaction of a compound of formula I with an inorganic or organic acid or base. Such salts are known as acid or base addition salts.

Examples of commonly used acids to form acid addition salts include inorganic acids such as hydrochloric acid, hydrobromic acid, hydroiodic acid, sulfuric acid, phosphoric acid and the like, and organic acids such as p-toluene sulfonic acid, methanesulfonic acid, oxalic acid, p-bromophenylsulfonic acid, carbonic acid, succinic acid, citric acid, benzoic acid, acetic acid and the like.

Example of commonly used bases to form base addition salts include inorganic bases such as ammonium hydroxide, ammonium carbonate, ammonium hydrogen carbonate, alkaline metal or alkaline earth metal hydroxides or carbonates and the like, and organic bases such as aliphatic amines, primary, secondary and tertiary amines, and aliphatic diamines and the like.

In general, the above pharmaceutically acceptable acid or base addition salts can be obtained by the reaction of a compound of formula I with equimolar or excess amount of an acid or base.

The compound of the invention can be essentially prepared by the process described in the Japanese Patent Publication No. 211819/1994, the disclosure of which is herein incorporated by reference. However, the present invention is by no means limited by the process per se. One process for the production of the compounds of the invention is exemplified in the following Preparations.

Scheme I

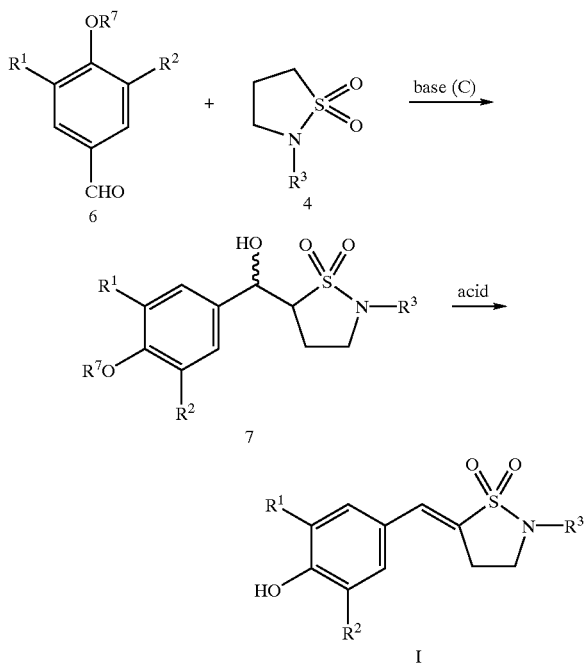

In the above formulae, $R^1$, $R^2$, and $R^3$ are as defined above and $R^7$ is hydrogen or a hydroxy-protecting group.

In the case that $R^7$ of the compound 6 is a hydroxy-protecting group, examples of the protecting group include methoxymethyl, methoxyethyl, trimethylsilyl, tert-butyldimethylsilyl. $R^7$ is preferably a hydroxy-protecting group, particularly methoxymethyl group.

One of the starting compounds for the above reaction, the sulfur-containing compound 4 can be prepared, for example, according to a reaction scheme below.

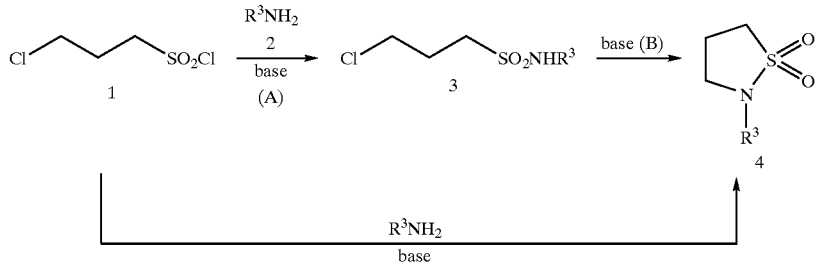

In the above formulae, $R^3$ is as defined above.

3-Chloropropylsulfonyl chloride 1 is reacted with amine 2 to yield sulfonamide intermediate 3.

The reaction is carried out in the presence of base (A), if necessary, in a solvent such as ether, chloroform, methylene chloride, dichloroethane, tetrahydrofuran, dimethoxyethane, diethoxyethane, benzene, toluene, xylene, ethyl acetate, methyl acetate and the like, which solvent may contain water. The amine ($R^3NH_2$) may be in the form of hydrochloride salt.

The base (A) used in the case of necessity includes alkali metal bases such as lithium hydroxide, sodium hydroxide, potassium hydroxide, sodium carbonate, potassium carbonate, sodium bicarbonate and potassium hydrogencarbonate and the like, and organic bases such as pyridine, 4-N,N-dimethylaminopyridine (DMAP), triethylamine, diisobutyl ethylamine, 1,8-diazabicyclo[5,4,0]undec-7-ene (DBU), 1,4-diazabicyclo[2,2,2]octane (DABCO) and the like. When an alkali metal base is used, it is preferable to add a phase transfer catalyst, if necessary. Examples of preferred phase transfer catalysts are quaternary ammonium salts such as N-benzyltrimethylammonium salts, tetrabutylammonium salts and the like.

The reaction for converting sulfonamide intermediate 3 into sulfur-containing heterocyclic compound 4 can be carried out in the presence of a base (B) in a solvent as described above, while anhydrous solvents such as dimethyl sulfoxide, dimethylformamide and the like may also be used and rather preferable. Sodium hydride and lithium hydride can be used as a base B as well as those described above.

Alternatively, sulfur-containing compound 4 can be prepared directly from compound 1 without separation of sulfonamide intermediate 3. In this case, the reaction of compound 1 with amine 2 is carried out in a suitable solvent in the presence of two equivalents of a base. The solvent and the base may be selected from those exemplified above but it is particularly preferable to use sodium hydride as a base and dimethylformamide as a solvent.

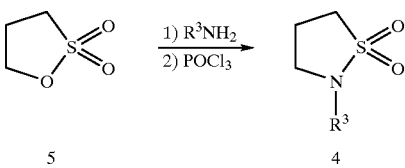

Alternatively, the desired sulfur-containing compound 4 can also be obtained from commercially available γ-sultone 5. (See "Preparation"). Briefly, compound 5 is allowed to react with amine ($R^3NH_2$) and the resultant product is then treated with a dehydrating agent. The reaction can be carried out without solvent but may be conducted in a solvent described above, if necessary. Commonly used reagent such as phosphorus oxychloride, thionyl chloride, phosphorus pentachloride, phosphorus pentoxide and the like may be used as a dehydrating agent, and phosphorus oxychloride is particularly preferable.

The aldol reaction between compounds 6 and 4 obtained above is carried out in the presence of a base (C) in a suitable solvent. Examples of base (C) include organic lithium salts such as n-butyllithium, sec-butyllithium, tert-butyllithium, phenyllithium, lithium diisopropylamide, lithium diethylamide, lithium hexamethyldisilazane and the like, and alkali metal bases such as sodium hydride and potassium tert-butoxide and the like. Particularly, lithium diisopropylamide or lithium hexamethyldisilazane is preferable.

Examples of reaction solvents include ether solvents such as diethyl ether, tetrahydrofuran (THF), dimethoxyethane, diethoxyethane and the like or hydrocarbon solvents such as n-hexane, cyclohexane and the like. The reaction is preferably conducted in the presence of a reagent that serves as a ligand of lithium metal, for example tetramethylethylenediamine, hexamethylphosphoramide and the like, if necessary.

The reaction is carried out at temperature ranging from −80° C. to +50° C. with preference in lower temperature range.

Aldol adduct 7 is converted to compound I in the presence of an acid. Examples of acids include organic acids such as trifluoroacetic acid, p-toluenesulfonic acid, camphorsulfonic acid and the like and inorganic acids such as sulfuric acid, hydrochloric acid and the like. Further, ordinary dehydrating agents such as thionyl chloride, methanesulfonyl chloride, aluminium chloride, phosphorus oxychloride, phosphorus pentachloride and the like can be used. Preferably, the reaction is carried out with heating in an aromatic hydrocarbon such as benzene, toluene, xylene and the like, a halogenated hydrocarbon such as chloroform, dichloromethane, dichloroethane and the like, or an ether solvent such as tetrahydrofuran, dimethoxyethane, diethoxyethane and the like.

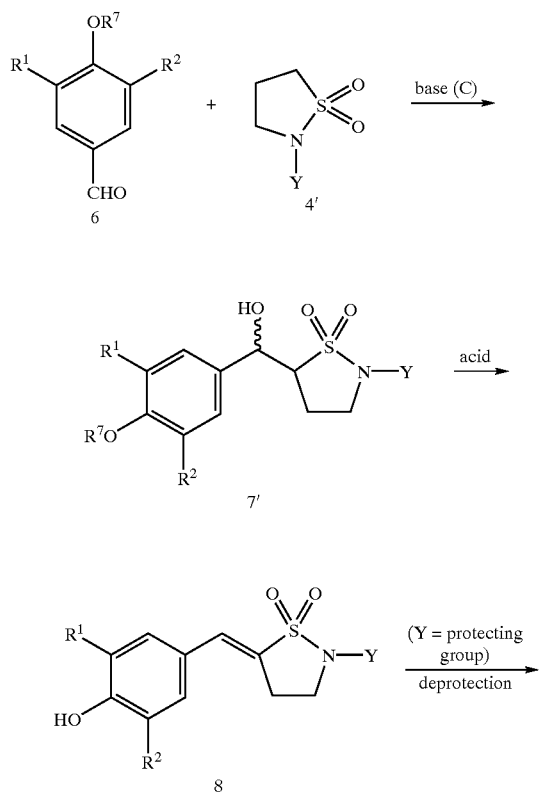

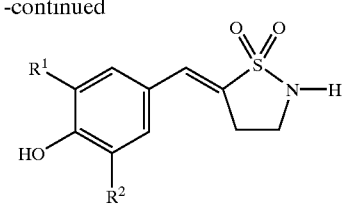

Base (C) in the above formula is as defined above. Y means an N-protecting group such as tert-butoxycarbonyl, benzyloxycarbonyl, benzyl, 4-methoxybenzyl, 3,4-dimethoxybenzyl, 4-nitrobenzyl and the like. The reaction conditions of the aldol reaction are similar to those described in the reaction scheme I above. Dehydrating and deprotecting reagents used in the conversion of aldol adduct 7' to compounds 10 include p-toluenesulfonic acid and trifluoroacetic acid, aluminium chloride, titanium tetrachloride and the like. The conditions such as reaction solvent, temperature and the like are similar to those described in reaction scheme I. Compound 8 is deprotected to obtain compound 10, which is the compound of formula I wherein $R^3$ is hydrogen.

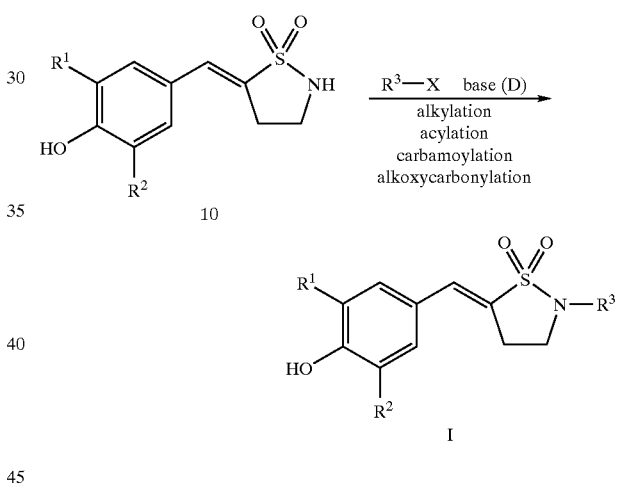

In this reaction, a desired substituent $R^3$ is added to compound 10 obtained in the above reaction scheme II, which corresponds to the compound of formula I wherein $R^3$ is hydrogen in the formula I, to yield various derivatives. Base (D) to be used when $R^3$—X is an alkylating agent includes alkali metal salts such as sodium hydroxide, potassium hydroxide, sodium carbonate, potassium carbonate, sodium bicarbonate, potassium hydrogen carbonate, lithium hydroxide and the like, or organic bases such as pyridine, triethylamine, diisopropylethylamine and the like. The alkylation is preferably carried out using sodium hydroxide or potassium carbonate in the presence of an appropriate quaternary ammonium salt as a phase transfer catalyst.

In the case where $R^3X$ is an acylating agent, an organic base such as pyridine, 4-dimethylaminopyridine, triethylamine, diisopropylethylamine or the like is preferably used as base (D).

When $R^3X$ is a carbamoylating agent or alkoxycarbonylating agent, an organic lithium base such as n-butyllithium, lithium hexamethyldisilazane, lithium diisopropylamide or the like is preferably utilized as base (D). The present invention is not limited to the use of these bases, and organic bases such as pyridine, triethylamine, diisopropylethylamine and the like or the alkali metal bases described above are also useable.

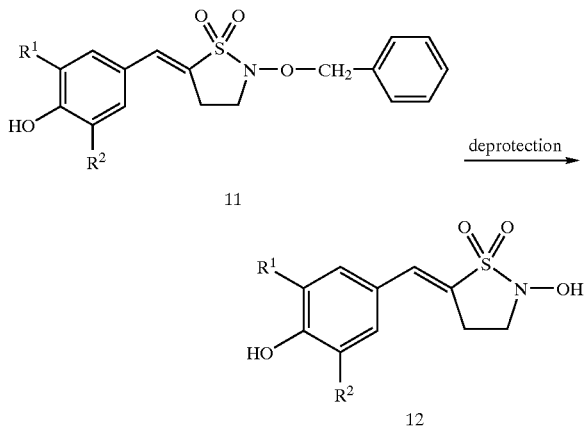

Scheme IV

Compounds 12, which corresponds to the compound of formula I wherein $R^3$ is OH, is obtained by de-benzylation of compounds 11. The de-benzylation is carried out using a deprotecting agent. The deprotection is conducted by hydrogenation in the presence of palladium on carbon or platinum oxide as catalyst, or by using a Lewis acid such as aluminium chloride, titanium tetrachloride or the like along with anisole, 2,6-di-tert-butylphenol and the like, if necessary.

Besides halogenated hydrocarbons such as dichloromethane, chloroform, dichloroethane and the like, nitromethane, benzene, toluene, xylene and the like can also be used as a reaction solvent.

The processes in the above schemes I, II and III are generally applicable to the production of compounds I of the invention, and they are specifically illustrated in Preparations 1–43 below.

The compound I of the present invention can be orally or parenterally administered as an anti-inflammatory agent. In the case of oral administration, a compound of the present invention may be formulated into ordinary formulations in the form of solid formulations such as tablets, powders, granules, capsules and the like; solutions; oily suspensions; or liquid formulations such as syrups, elixirs and the like. In the case of parenteral administration, a compound of the present invention may be formulated into an aqueous or oily suspension for injection or an external preparation. In preparing the formulations, conventional excipients, binders, lubricants, aqueous solvents, oily solvents, emulsifiers, suspending agents or the like may be used, and other additives, such as preservatives, stabilizers or the like may also be included.

Although appropriate daily dosage of the compound of the invention varies depending upon the administration route, age, body weight and conditions of a particular patient, and the kind of disease to be treated. In general, however, in the case of adult patients, it may be between 10–500 mg, preferably 50–100 mg for oral administration, and 1–250 mg, preferably 5–10 mg for parenteral administration, in 1–5 divisions.

The following Preparations and Examples are provided to further illustrate the present invention and are not to be construed as limiting thereof. The abbreviations used in the Preparations and Examples have the following meanings:

LDA: lithium diisopropylamide;
MOM: methoxymethyl;
p-TsOH: p-toluenesulfonic acid;
THF: tetrahydrofuran;
DMF: N,N-Dimethylformamide;
HMPA: hexamethylphosphoramide;
LiHMDS: lithium hexamethyldisilazane;
DBU: 1,8-diazabicyclo[5,4,0]undec-7-ene; and
DIBAL: diisobutylalminium hydride.

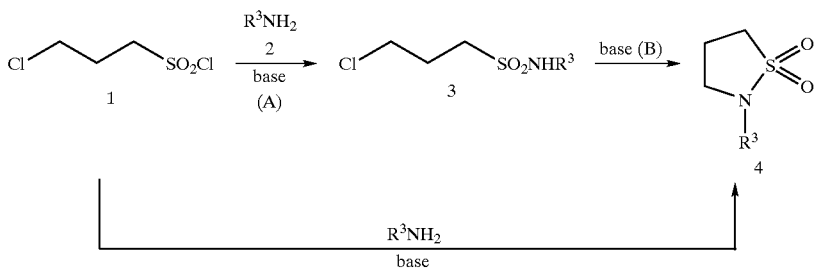

Preparation 1 ($R^3$=Et)

N-Ethyl-1,2-isothiazolidine-1,1-dioxide (4a)

To a solution of 3-chloropropylsulfonyl chloride 1 (6.1 g, 34.5 mmol) in ether (25 ml) was dropwise added ethylamine (a 70% aqueous solution, 4.4 g, 68.3 mmol) with stirring and ice-cooling over 15 minutes, and the resultant mixture was stirred for one hour at room temperature. The reaction mixture was concentrated in vacuo, Benzene (100 ml) was added to the residue, and the solvent was removed in vacuo. To the residue was added ether (150 ml) and filtered to remove the insoluble material. The filtrate was distilled in vacuo to remove ether and 6.96 g (yield, about 100%) of crude N-ethyl-3-chloro propylsulfonamide (intermediate 3a) was obtained as colorless crystals (m.p.=30–32° C.). To a solution of this intermediate 3a (6.96 g, 34.5 mmol) in THF (50 ml) was slowly added sodium hydride (60% in oil, 1.52 g, 38.0 mmol) with stirring under ice-cooling over 15 minutes. The reaction mixture was stirred for another 30 minutes at room temperature. After the addition of ether (50 ml), the mixture was filtered to remove insoluble material and the solvent was distilled in vacuo to give 4.93 g (96%) of the desired compound 4a as a pale yellow oil. IR $(CHCl_3)cm^{-1}$: 3018, 2976, 2868, 1452, 1306, 1220, 1179, 1129, 1015; NMR $(CDCl_3)$ δ: 1.24 (3H, t, J=7.4 Hz, $CH_3$), 2.28–2.42 (2H, m, $CH_2$), 3.10 (2H, q, J=7.4 z, $CH_2$), 3.15 (2H, t, J=7.6 Hz, $CH_2$), 3.22–3.29 (2H, m, $CH_2$).

Preparation 2 ($R^3$=Me)
N-Methyl-1,2-isothiazolidine-1,1-dioxide (4b)

3-Chloropropylsulfonyl chloride 1 (16.8 g, 94.9 mmol), ethylamine hydrochloride (13.5 g, 200 mmol), and potassium carbonate (27.6 g, 200 mmol) were sequentially added to ethyl acetate (500 ml). After the addition of N-benzyltrimethylammonium chloride (about 200 mg) to the mixture, the resultant mixture was stirred for 2 hours at room temperature and dried over anhydrous sodium sulfate. The mixture was filtered through a small amount of silica gel and the filtrate was concentrated in vacuo to give 12 g (74%) of crude N-methyl-3-chloropropylsulfonamide (intermediate 3b) as a pale yellow oil.

To a solution of said intermediate 3b (11.79 g, 68.69 mmol) in benzene (300 ml) was added DBU (10.79 ml, 72.12 mmol), and the resultant mixture was stirred for 24 hours at room temperature and filtered through a small amount of silica gel. The solvent was removed to give 7.0 g (75%) of the desired compound 4b as a colorless solid (m.p.=36–40° C.). IR (CHCl$_3$)cm$^{-1}$: 3016, 1451, 1307, 1218, 1187, 1127; NMR (CDCl$_3$) δ: 2.27–2.42 (2H, m, CH$_2$), 2.69 (3H, s, CH$_3$), 3.11–3.20 (2H, m, CH$_2$), 3.22 (2H, t, J=6 .Hz, CH$_2$).

Preparation 3 ($R^3$=CH$_2$CH(CH$_3$)$_2$)
N-Isobutyl-1,2-isothiazolidine-1,1-dioxide (4c)

3-Chloropropylsulfonyl chloride 1 (7.08 g, 40 mmol), isobutylamine (7.3 g, 100 mmol) and sodium bicarbonate (3.36 g, 40 mmol) were sequentially added to a mixture of ethyl acetate (200 ml) and water (20 ml). To the mixture was added N-benzyltrimethylammonium chloride (about 100 mg), and the resultant mixture was stirred for 3 hours at room temperature and then treated in a manner described in Preparation 2 to give 8.19 g (96%) of crude N-isobutyl-3-chloropropylsulfonamide (intermediate 3c) as colorless crystals (m.p.=68–69° C.).

To a solution of said intermediate 3c (4.27 g, 20 mmol) in benzene (60 ml) was added DBU (3.3 ml, 22 mmol), and the reaction mixture was treated in a manner as described in Preparation 2 to give 3.37 g (95%) of the desired compound 4c as a colorless oil. IR (CHCl$_3$)cm$^{-1}$: 3016, 2956, 1465, 1304, 1226, 1131, 1024; NMR (CDCl$_3$) δ: 0.95 (6H, d, J=6.6 Hz, (CH$_3$)$_2$), 1.75–1.96 (1H, m, CH), 2.27–2.42 (2H, m, CH$_2$), 2.80 (2H, d, J=7.4 Hz, CH$_2$), 3.10–3.19 (2H, m, CH$_2$), 3.24 (2H, t, J=6.8 Hz, CH$_2$).

Preparation 4 ($R^3$=cyclopropyl)
N-Cyclopropyl-1,2-isothiazolidine-1,1-dioxide (4d)

3-chloropropylsulfonyl chloride 1 (7.08 g, 40 mmol), cyclopropylamine (6.0 g, 105 mmol) and sodium bicarbonate (3.7 g, 44 mmol) were treated in a mixture of ether (200 ml) and water (10 ml) in a manner as described in Preparation 3 to give 8.0 g (about 100%) of crude N-cyclopropyl-3-chloropropylsulfonamide (intermediate 3d) as crystals (m.p.=48–49.5° C.).

Said intermediate 3d (1.98 g, 10 mmol) was reacted with DBU (1.65 ml, 11 mmol) in benzene (30 ml) in a manner as described in Preparation 2 to give 1.40 g (87%) of the desired compound 4d as a pale yellow oil. IR (CHCl$_3$)cm$^{-1}$: 3016, 1309, 1221, 1140, 1026; NMR (CDCl$_3$) δ: 0.60–0.85 (4H, m, cyclopropyl), 2.20–2.40 (2H, m, CH$_2$), 3.15–3.25 (3H, m, CH$_2$+CH), 3.32 (2H, t, J=6.6 Hz, CH$_2$).

Preparation 5 ($R^3$=—CH$_2$CH$_2$CH$_3$)
N-n-Propyl-1,2-isothiazolidine-1,1-dioxide (4e)

3-chloropropylsulfonyl chloride 1 (7.08 g, 40 mmol), n-propylamine (5.90 g, 100 mmol), potassium carbonate (5.52 g, 40 mmol) and a small amount of N-benzyltrimethylammonium chloride (about 100 mg) were stirred in a mixture of ether (200 ml) and water (20 ml) for 3 hours, the reaction mixture was then treated in a manner as described in Preparation 2 to give 8.0 g (about 100%) of crude N-n-propyl-3-chloropropylsulfonamide (intermediate 3e) as crystals (m.p.=47.5–48° C.).

Said intermediate 3e (2.0 g, 10 mmol) was reacted with DUB (1.65 ml, 11 mmol) in benzene (30 ml) in a manner as described in Preparation 2 to give 1.41 g (86%) of the desired compound 4e as a pale yellow to colorless oil. IR (CHCl$_3$)cm$^{-1}$: 3018, 2962, 2868, 1304, 1224, 1130, 1019; NMR (CDCl$_3$) δ: 0.96 (3H, t, J=7 Hz, CH$_3$), 1.52–1.72 (2H, m, CH$_2$), 2.28–2.42 (2H, m, CH$_2$), 2.94–3.04 (2H, m, CH$_2$), 3.10–3.20 (2H, m, CH$_2$), 3.25 (2H, t, J=6.7 Hz, CH$_2$).

Preparation 6 ($R^3$=OCH$_3$)
N-Methoxy-1,2-isothiazolidine-1,1-dioxide (4f)

3-Chloropropylsulfonyl chloride 1 (7.08 g, 40 mmol), O-methylhydroxylamine hydrochloride (3.76 g, 40 mmol), and potassium carbonate (5.80 g, 42 mmol) were reacted in a manner as described in Preparation 5 to give 7.02 g (94%) of crude N-methoxy-3-chloropropylsulfonamide (intermediate 3f) as a colorless to pale yellow oil.

The intermediate 3f (6.25 g, 33.3 mmol) was reacted with sodium hydride (60% in oil, 1.47 g, 36.7 mmol) in a manner as described in Preparation 1 to give 3.70 g (73%) of the desired compound 4f as a colorless oil. IR (CHCl$_3$)cm$^{-1}$: 3022, 1355, 1249, 1222, 1165, 1138, 1035, 1011; NMR (CDCl$_3$) δ: 2.37–2.50 (2H, m, CH$_2$), 3.20–3.14 (2H, m, CH$_2$), 3.50 (2H, t, J=7.0 Hz, CH$_2$), 3.81 (3H, s, OCH$_3$).

Preparation 7 ($R^3$=OCH$_2$C$_6$H$_5$)
N-Benzyloxy-1,2-isothiazolidine-1,1-dioxide (4g)

3-Chloropropylsulfonyl chloride 1 (30.28 g, 0.17 mol), O-benzylhydroxylamine hydrochloride (27.3 g, 0.17 mol), potassium carbonate (50 g, 0.36 mol) and tetrabutylammonium sulfate (about 500 mg) are reacted in a mixture of ether (1L) and water (100 ml) for 24 hours at room temperature and the reaction mixture was extracted with ethyl acetate. The extract was subjected to column chromatography on silica gel. From the fraction eluted with a mixture of ethyl acetate/n-hexane (1:4), 18.4 g (41%) of crude N-benzyloxy-3-chloropropylsulfonamide (intermediate 3g) was obtained as a pale yellow oil.

To a solution of the above intermediate 3g (18.4 g, 69.9 mmol) in THF (150 ml) was added sodium hydride (60% in oil, 2.94 g, 73.4 mmol) and the reaction was carried out in a manner as described in Preparation 1. The product was subjected to column chromatography on silica gel. From the fraction eluted with a mixture of ethyl acetate/n-hexane (1:5), 10.75 g (68%) of the desired compound 4g was obtained as a colorless crystal. M.p.=52–54° C. IR (CHCl$_3$) cm$^{-1}$: 3022, 2956, 1453, 1354, 1165, 1140, 1081, 1000; NMR(CDCl$_3$) δ: 2.30–2.48 (2H, m, CH$_2$), 3.04–3.14 (2H, m, CH$_2$), 3.45 (2H, t, J=6.9 Hz, CH$_2$), 5.00 (2H, s, OCH$_2$), 7.30–7.45 (5H, m, C$_6$H$_5$).

Preparation 8 ($R^3$=4-methoxybenzyl)
N-(4-Methoxybenzyl)-1,2-isothiazolidine-1,1-dioxide (4h)

3-Chloropropylsulfonyl chloride 1 (17.7 g, 0.1 mol), p-methoxybenzylamine (15.0 g, 0.11 mol), and sodium bicarbonate (8.4 g, 0.1 mol) were reacted in a mixture of ethyl acetate (400 ml) and water (40 ml) in a manner as described in Preparation 3 to give 19.1 g (69%) of crude N-(4-methoxybenzyl)-3-chloropropylsulfonamide (intermediate 3h) as colorless crystals. M.p.=78–80° C.

The above intermediate 3h (11.11 g, 40 mmol) was reacted with DBU (6.6 ml, 40 mmol) in benzene (150 ml). The resultant mixture was treated in a manner as described in Preparation 2 to give 8.89 g (92%) of the desired compound 4h as crystals. M.p.=48–51° C. IR (CHCl$_3$)cm$^{-1}$: 3016, 1612, 1511, 1304, 1245, 1136, 1034. NMR (CDCl$_3$)

δ: 2.20–2.38 (2H, m, CH$_2$), 3.09 (2H, t, J=6.8 Hz, CH$_2$), 3.14–3.24 (2H, m, CH$_2$), 3.81 (3H, s, OCH$_3$), 4.12 (2H, s, CH$_2$), 6.84–6.94 (2H, m, CH$_2$), 7.22–7.32 (4H, m, 4×aromatic-H).

Preparation 9 (R$^3$=3,4-dimethoxybenzyl)

N-(3,4-Dimethoxybenzyl)-1,2-isothiazolidine-1,1-dioxide (4i)

3-Chloropropylsulfonyl chloride 1 (8.85 g, 50 mmol), 3,4-dimethoxybenzylamine (9.0 ml, 60 mmol) and potassium carbonate (4.14 g, 30 mmol) were treated in a manner as described in Preparation 2 to give 14.5 g (94%) of crude N-(3,4-dimethoxybenzyl)-3-chloropropylsulfonamide (intermediate 3i). From the intermediate 3i, the desired compound 4i (yield: 69%) was yielded in a manner as described in Preparation 1. IR (CHCl$_3$)cm$^{-1}$: 3018, 1516, 1307, 1262, 1225, 1155, 1138, 1027. NMR (CDCl$_3$) δ: 2.22–2.38 (2H, m, CH$_2$), 3.11 (2H, t, J=6.7 Hz, CH$_2$), 3.16–3.25 (2H, m, CH$_2$), 3.88 (3H, s, OCH$_3$), 3.89 (3H, s, OCH$_3$), 4.12 (2H, s, CH$_2$), 6.79–6.91 (3H, m, 3×aromatic-H).

Preparation 10 (R$^3$=C$_6$H$_5$)

N-Phenyl-1,2-isothiazolidine-1,1-dioxide (4j)

3-Chloropropylsulfonyl chloride 1 (1.456 g, 8.23 mmol) was dropwise added to a solution of aniline (0.5 ml, 8.23 mmol) in pyridine (5 ml) with cooling at −20° C. to −30° C. over about 5 minutes. After the completion of the addition, the reaction mixture was stirred for another 45 minutes at room temperature. The reaction mixture was concentrated in vacuo and the residue was subjected to column chromatography on silica gel. From the fraction eluted with a mixture of ethyl acetate/n-hexane (1:2), 1.683 g (88%) of N-phenyl-3-chloropropylsulfonamide (intermediate 3j) was obtained as a yellow oil. From the intermediate 3j, the desired compound 4j (yield: 57%) was yielded as a pale yellow solid in a manner as described in Preparation 1. IR (CHCl$_3$)cm$^{-1}$: 3020, 1598, 1495, 1315, 1139. NMR (CDCl$_3$) δ: 2.46–2.60 (2H, m, CH$_2$), 3.34–3.42 (2H, m, CH$_2$), 3.78 (2H, t, J=6.6 Hz, CH$_2$), 7.10–7.40 (5H, m, C$_6$H$_5$).

Preparation 11 (R$^3$=4-chlorophenyl)

N-(4-Chlorophenyl)-1,2-isothiazolidine-1,1-dioxide (4k)

According to a similar method to that of Preparation 10, 3-chloropropylsulfonyl chloride was reacted with 4-chloroaniline in pyridine to give N-(4-chlorophenyl)-3-chloropropylsulfonamide (intermediate 3k) (yield 93%). From the intermediate 3k, the desired compound 4k (yield: 68%) was yielded as colorless crystals (m.p.=110.5–111.5° C.) in a manner as described in Preparation 1. IR (KBr)cm$^{-1}$: 3010, 2960, 1595, 1493, 1300, 1267, 1131. NMR (CDCl$_3$) δ: 2.47–2.61 (2H, m, CH$_2$), 3.35–3.43 (2H, m, CH$_2$), 3.76 (2H, t, J=6.4 Hz, CH$_2$), 7.16–7.36 (4H, m, 4×aromatic-H).

Preparation 12 (R$^3$=2-pyridyl)

N-(2-Pyridyl)-1,2-isothiazolidine-1,1-dioXide (4l)

According to a similar method to that of Preparation 10, 3-chloropropylsulfonyl chloride was reacted with 2-aminopyridine to give N-(2-pyridyl)-3-chloropropylsulfonamide (intermediate 3l) as a pale yellow solid (yield 54%). To a solution of this intermediate 3l (2.138 g, 9.11 mmol) in DMF (30 ml) was added sodium hydride (60% in oil, 401 mg, 10 mmol) under ice-cooling. The resultant mixture was stirred for 30 minutes at 85° C. and the solvent was removed in vacuo. The residue was subjected to column chromatography on silica gel. From the fraction eluted with a mixture of ethyl acetate/n-hexane (1:1), 1.806 g (100%) of the desired compound 4l was obtained as a yellow solid. IR (CHCl$_3$)cm$^{-1}$: 3022, 1592, 1473, 1434, 1139. NMR (CDCl$_3$) δ: 2.47–2.60 (2H, m, CH$_2$), 3.43 (2H, t, J=7.5 Hz, CH$_2$), 4.05 (2H, t, J=6.6 Hz, CH$_2$), 6.88–7.02 (1H, m, CH), 7.26–7.35 (1H, m, CH), 7.58–7.70 (1H, m, CH), 8.33 (1H, d, J=4.4 Hz, CH).

Preparation 13 (R$^3$=3-pyridyl)

N-(3-Pyridyl)-1,2-isothizolidine-1,1-dioxide (4m)

According to a similar method to that of Preparation 10, 3-chloropropylsulfonyl chloride 1 (7.28 g, 41.1 mmol) was reacted with 3-aminopyridine (4.6 g, 49.3 mmol) in pyridine (15 ml) to give 4.50 g (46%) of crude N-(3-pyridyl)-3-chloropropylsulfonamide (intermediate 3m) as a colorless solid.

The intermediate 3m (232 mg, 0.988 mmol) was treated with sodium hydride (60% in oil, 43.5 mg, 1.09 mmol) in DMF (5 ml) in a similar manner as described in Preparation 12 to give 190 mg (97%) of the desired compound 4m as a colorless solid. IR (CHCl$_3$)cm$^{-1}$: 3022, 2960, 1590, 1484, 1428, 1319, 1142. NMR (CDCl$_3$) δ: 2.53–2.67 (2H, m, CH$_2$), 3.38–3.45 (2H, m, CH$_2$), 3.83 (2H, t, J=6.6 Hz, CH$_2$), 7.28–7.36 (1H, m, CH), 7.73–7.79 (1H, m, CH), 8.41 (1H, d, J=4.6 Hz, CH), 8.46 (1H, d, J=2.4 Hz, CH).

Preparation 14 (R$^3$=4-pyridyl)

N-(4-Pyridyl)-1,2-isothiazolidine-1,1-dioxide (4n)

To a solution of 3-chloropropylsulfonyl chloride 1 (3 ml, 24.7 mmol) and 4-aminopyridine (2.32 g, 24.7 mmol) in DMF (25 ml) was slowly added sodium hydride (60% in oil, 2.17 g, 54.3 mmol) over about 5 minutes with stirring under ice-cooling. The stirring was then continued for another 30 minutes at 50° C. The reaction mixture was concentrated in vacuo, the residue was subjected to column chromatography on silica gel. From the fraction eluted with a mixture of methylene chloride/methanol (10:1), 1.294 (27%) of the desired compound 4n was obtained as a yellow solid. IR (ClCl$_3$)cm$^{-1}$: 3024, 2956, 1597, 1504, 1320, 1143. NMR (CDCl$_3$) δ: 2.53–2.67 (2H, m, CH$_2$), 3.43 (2H, t, J=7.6 Hz, CH$_2$), 3.81 (2H, t, J=6.6 Hz, CH$_2$), 7.08 (2H, d, J=5.4 Hz, CH), 8.49 (2H, d, J=5.4 Hz, CH).

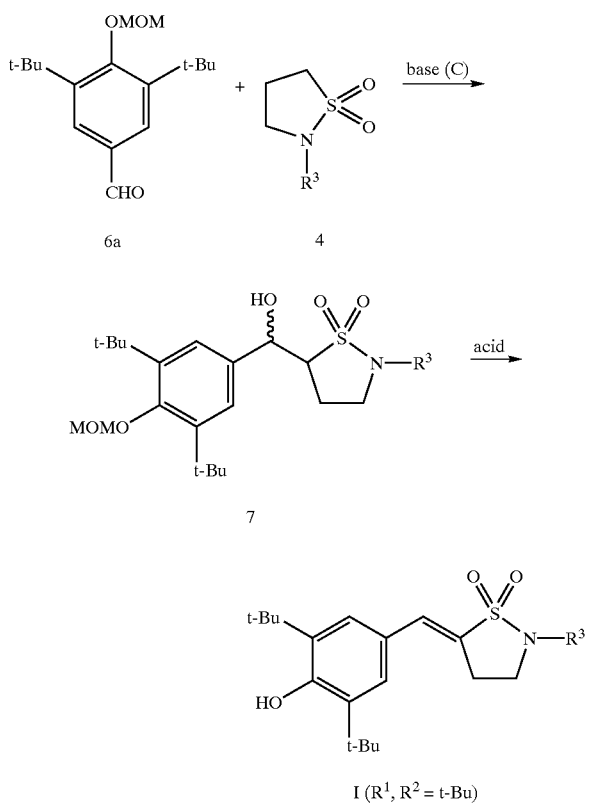

Preparation 15 ($R^3$=Et)

(E)-2-Ethyl-5-(3,5-di-tert-butyl-4-hydroxy)benzylidene-1,2-isothiazolidine-1,1-dioxide (Ia)

To diisopropylamine (15.5 ml, 110.6 mmol) was dropwise added in an ice-water bath n-butyllithium in n-hexane (1.6 M, 69.5 ml, 111 mmol) over 20 minutes with stirring. After completion of the addition, stirring was conducted for another 15 minutes. The reaction mixture was cooled to −78° C. and added THF (100 ml). To the reaction mixture was dropwise added a solution of N-ethyl-1,2-isothiazolidine-1,1-dioxide 4a (15 g, 100.5 mmol), 3,5-di-tert-butyl-4-methoxymethoxybenzaldehyde 6a (25 g, 90.5 mmol) and HMPA (30 ml) in the THF (70 ml) over 15 minutes with stirring. The reaction mixture was stirred for another 30 minutes at the same temperature, warmed to room temperature, poured into cold 2N HCl (100 ml) and extracted with ethyl acetate (2×250 ml). The ethyl acetate phase was washed with a dilute aqueous solution of sodium bicarbonate (300 ml) and a saturated brine (300 ml), dried over anhydrous sodium sulfate. The solvent was removed in vacuo, and the residue was subjected to column chromatography on silica gel eluting with n-hexane/ethyl acetate (4:1 to 1:1) to give 21.3 g (55%) of aldol adduct 7a as a colorless solid.

To a solution of the aldol adduct 7a (8.5 g, 19.9 mmol) in toluene (150 ml) was added p-toluenesulfonic acid hydrate (2.49 g, 13 mmol). The resultant mixture was heated to reflux for 30 minutes and then poured into a dilute aqueous solution of sodium bicarbonate (150 ml) and extracted with ethyl acetate (150 ml×2). The organic layer was washed with water (150 ml) and a saturated brine (150 ml), dried over anhydrous sodium sulfate. The solvent was removed in vacuo, and the residue was subjected to column chromatography on silica gel. From the fraction eluted with n-hexane/ethyl acetate (3:1), the desired compound Ia (2.59 g, 36%) was yielded. M.p.=135–137° C. IR (KBr)cm$^{-1}$: 3610, 3440, 2970, 2880, 1645, 1597, 1430, 1290, 1173, 1151, 1139. NMR (CDCl$_3$) δ: 1.29 (3H, t, J=7.2 Hz, CH$_3$), 1.45 (18H, s, 2×But), 3.07–3.19 (4H, m, CH$_2$), 3.28 (2H, q, J=7.2 Hz, CH$_2$), 5.50 (1H, s, OH), 7.24–7.26 (3H, m, 2×aromatic-H, CH). Elementary analysis (C$_{20}$H$_{31}$NO$_3$S) Calcd: C, 65.71; H, 8.55; N, 3.83; S, 8.77. Found: C, 65.65; H, 8.43; N, 3.85; S, 8.78.

Preparation 16 ($R^3$=CH$_3$)

(E)-2-Methyl-5-(3,5-di-tert-butyl-4-hydroxy)benzylidene-1,2-isothiazolidine-1,1-dioxide (Ib)

According to a similar method to that of Preparation 15, an aldol reaction was carried out using compound 6a (3.34 g, 12 mmol) and N-methyl-1,2-isothiazolidine-1,1-dioxide 4b (1.35 g, 10 mmol) to give 1.65 g (40%) of adduct 7b. To a solution of the adduct 7b (1.60 g, 3.87 mmol) in toluene (30 ml) was added p-toluenesulfonic acid hydrate (160 mg) and the resultant mixture was heated to reflux for 30 minutes. The reaction product was subjected to column chromatography on silica gel. From the fraction eluted with a mixture of n-hexane/ethyl acetate (3:7), the desired compound Ib (580 mg, 43%) was obtained.

M.p.=168–170° C. IR (CHCl$_3$)cm$^{-1}$: 3620, 2956, 1435, 1292, 1218, 1149. NMR (CDCl$_3$) δ: 1.45 (18H, s, 2×But), 2.76 (3H, s, NCH$_3$), 3.07–3.18 (2H, m, CH$_2$), 3.20–3.32 (2H, m, CH$_2$), 5.51 (1H, s, OH), 7.23–7.29 (3H, m, 2×aromatic-H, CH). Elementary analysis (C$_{19}$H$_{29}$NO$_3$S) Calcd: C, 64.92; H, 8.32; N, 3.98; S, 9.12. Found: C, 64.62; H, 8.31; N, 3.95; S, 9.14.

Preparation 17 ($R^3$=CH$_2$CH(CH$_3$)$_2$)

(E)-2-Isobutyl-5-(3,5-di-tert-butyl-4-hydroxy)benzylidene-1,2-isothiazolidine-1,1-dioxide (Ic)

According to a similar method to that of Preparation 15, an aldol reaction was carried out using compound 6a (2.78 g, 10 mmol) and N-isobutyl-1,2-isothiazolidine-1,1-dioxide 4c (1.95 g, 11 mmol) to give 3.67 g (81%) of adduct 7c.

This adduct 7c (3.60 g, 7.9 mmol) was treated in toluene (50 ml) with p-toluenesulfonic acid hydrate (360 mg) in a similar manner as that of Preparation 15. The product was subjected to column chromatography on silica gel. From the fraction eluted with a mixture of n-hexane-ethyl acetate (1:3), the desired compound Ic (1.30 g, 42%) was obtained. M.p.=167–170° C. IR (CHCl$_3$)cm$^{-1}$: 3620, 2956, 1646, 1435, 1289, 1240, 1148, 1081. NMR (CDCl$_3$) δ: 0.97 (6H, d, J=6.4 Hz, (CH$_3$)$_2$), 1.45 (18H, s, 2×But), 1.81–2.02 (1H, m, CH), 2.87 (2H, d, J=7.4 Hz, CH$_2$), 3.06–3.18 (2H, m CH$_2$), 3.22–3.33 (2H, m, CH$_2$), 5.50 (1H, s, OH), 7.23–7.27 (3H, m, 2×aromatic-H, CH).

Elementary analysis (C$_{22}$H$_{35}$NO$_3$S) Calcd: C, 67.14; H, 8.96; N, 3.56; S, 8.15. Found: C, 66.85; H, 8.99; N, 3.58; S, 8.11.

Preparation 18 ($R^3$=cyclopropyl)

(E)-2-Cyclopropyl-5-(3,5-di-tert-butyl-4-hydroxy)benzylidene-1,2-isothiazolidine-1,1-dioxide (Id)

According to a similar method to that of Preparation 15, an aldol reaction was carried out using compound 6a (2.67 g, 9.6 mmol) and N-cyclopropyl-1,2-isothiazolidine-1,1-dioxide 4d (1.29 g, 8.0 mmol) to give 3.09 g (88%) of adduct 7d. The adduct 7d (3.0 g, 7 mmol) was treated in toluene (50 ml) together with p-toluenesulfonic acid hydrate (300 mg). The reaction product was purified in a similar manner as that of Preparation 17 to give 1.03 g (40%) of the desired compound Id. M.p.=202–204° C. IR (CHCl$_3$)cm$^{-1}$: 3620, 2956, 1434, 1297, 1237, 1145. NMR (CDCl$_3$) δ: 0.68–0.90 (4H, m, 2×CH$_2$), 1.44 (18H, s, 2×But), 2.28–2.40 (1H, m, CH), 3.08 (2H, dt, J=2.6, 6.7 Hz, CH$_2$), 3.36 (2H, t, J=6.7 Hz, CH$_2$), 5.51 (1H, s, OH), 7.20–7.25 (3H, m, 2×aromatic-H, CH). Elementary analysis (C$_{21}$H$_{31}$NO$_3$S) Calcd: C, 66.81; H, 8.28; N, 3.71; S, 8.49. Found: C, 66.67; H, 8.29; N, 3.71; S, 8.38.

Preparation 19 ($R^3$=CH$_2$CH$_2$CH$_3$)

(E)-2-n-Propyl-5-(3,5-di-tert-butyl-4-hydroxy)benzylidene-1,2-isothiazolidine-1,1-dioxide (Ie)

According to a similar method to that of Preparation 15, an aldol reaction was carried out using compound 6a (2.78 g, 10 mmol) and N-n-propyl-1,2-isothiazolidine-1,1-dioxide 4e (1.35 g, 8.27 mmol) to give 1.5 g (41%) of adduct 7e. The adduct 7e was treated with p-toluenesulfonic acid hydrate (400 mg) in a manner as described in Preparation 15. The reaction product was subjected to column chromatography on silica gel. From the fraction eluted with a mixture of n-hexane-ethyl acetate (1:4), the desired compound Ie (810 mg, 26%) was obtained. M.p.=181–183° C. IR (CHCl$_3$)cm$^{-1}$: 3616, 2954, 1435, 1289, 1146. NMR (CDCl$_3$) cm$^{-1}$: 0.98 (3H, t, J=7.4 Hz, CH$_3$), 1.45 (18H, s, 2×But), 1.57–1.78 (2H, m, CH$_2$), 2.98–3.20 (4H, m, 2×CH$_2$), 3.22–3.34 (2H, m, CH$_2$), 5.50 (1H, s, OH), 7.23–7.27 (3H, m, 2×aromatic-H, CH). Elementary analysis (C$_{21}$H$_{33}$NO$_3$S) Calcd: C, 66.45; H, 8.76; N, 3.69; S, 8.45. Found: C, 66.25; H, 8.74; N, 3.70; S, 8.33.

Preparation 20 ($R^3$=OCH$_3$)

(E)-2-Methoxy-5-(3,5-di-tert-butyl-4-hydroxy)benzylidene-1,2-isothiazolidine-1,1-dioxide (If) and its (Z)-isomer (9f)

According to a similar method to that of Preparation 15, an aldol reaction was carried out using compound 6a (5.56 g, 20 mmol) and N-methoxy-1,2-isothiazolidine-1,1-dioxide 4f (3.32 g, 22 mmol) to give 6.89 g (80%) of adduct 7f. The adduct 7f (6.89 g, 16 mmol) was treated in toluene (100 ml) with p-toluenesulfonic acid hydrate (1 g) in a manner as described in Preparation 15. The reaction product was subjected to column chromatography on silica gel. From the fraction eluted with a mixture of n-hexane-ethyl acetate (6:1), the desired compound If (2.40 g, 41%) was obtained. M.p.=166–168° C. IR (CHCl$_3$)cm$^{-1}$: 3616, 2952, 1639, 1436, 1340, 1240, 1158, 1002. NMR (CDCl$_3$) δ: 1.45 (18H, s, 2×But), 3.11 (2H, dt, J=2.2, 7.0 Hz, CH$_2$), 3.66 (2H, t, J=7 Hz, CH$_2$), 3.81 (3H, s, OCH$_3$), 5.55 (1H, s, OH), 7.25–7.35 (3H, m, 3×aromatic-H, CH). Elementary analysis (C$_{19}$H$_{29}$NO$_4$S) Calcd: C, 62.10; H, 7.95; N, 3.81; S, 8.72. Found: C, 61.90; H, 7.88; N, 3.91; S, 8.67.

Preparation 21 (R$^3$=OCH$_2$C$_6$H$_5$)
(E)-2-Benzyloxy-5-(3,5-di-tert-butyl-4-hydroxy) benzylidene-1,2-isothiazolidine-1,1-dioxide (Ig)

According to a similar method to that of Preparation 15, an aldol reaction was carried out using compound 6a (15 g, 54 mmol) and N-benzyloxy-1,2-isothiazolidine-1,1-dioxide 4g (10.23 g, 45 mmol) to give 15.51 g (68%) of adduct 7g. The adduct 7g (10.21 g, 20.2 mmol) was treated in toluene (150 ml) with p-toluenesulfonic acid hydrate (1 g) in a manner as described in Preparation 15. The reaction product was filtered through a small amount of silica gel, and the filtrate was concentrated in vacuo to give 5.32 g (59%) of the desired compound Ig. M.p.=134–135° C. IR (CHCl$_3$)cm$^{-1}$: 3620, 2956, 1639, 1436, 1339, 1241, 1159. NMR (CDCl$_3$) δ: 1.44 (18H, s, 2×But), 3.09 (2H, dt, J=2.6, 6.8 Hz, CH$_2$), 3.58 (2H, t, J=6.8 Hz, CH$_2$), 5.02 (2H, s, OCH$_2$), 5.53 (1H, s, OH), 7.25–7.45 (8H, m, 7×aromatic-H, CH). Elementary analysis (C$_{25}$H$_{33}$NO$_4$S) Calcd: C, 67.69; H, 7.50; N, 3.16; S, 7.23. Found: C, 67.52; H, 7.59; N, 3.18; S, 7.16.

Preparation 22 (R$^3$=4-methoxybenzyl)
(E)-2-(4-Methoxybenzyl)-5-(3,5-di-tert-butyl)benzylidene-1,2-isothiazolidine-1,1-dioxide (Ih)

According to a similar method to that of Preparation 15, an aldol reaction was carried out using compound 6a (9 g, 32 mmol) and N-(4-methoxybenzyl)-1,2-isothiazolidine-1, 1-dioxide 4h (7.24 g, 30 mmol) to give 13.61 g (84%) of adduct 7h. The adduct 7h (12.6 g, 24.2 mmol) was treated in toluene (150 ml) with p-toluenesulfonic acid hydrate (1.3 g) in a manner as described in Preparation 15 to give 8.83 g of the desired compound Ih.

Preparation 23 (R$^3$=3,4-dimethoxybenzyl)
(E)-2-(3,4-Dimethoxybenzyl)-5-(3,5-di-tert-butyl-4-hydroxy)benzylidene-1,2-isothiazolidine-1,1-dioxide (Ii)

According to a similar method to that of Preparation 15, an aldol reaction was carried out using compound 6a (5.6 g, 20 mmol) and N-(3,4-dimethoxy)benzyl-1,2-isothiazolidine-1,1-dioxide 4i (5.85 g, 21.6 mmol) to give 9.25 g (78%) of adduct 7i. From the adduct 7i (4 g, 7.3 mmol), the desired compound Ii (2.5 g) was obtained by dehydration and deprotection in a manner as described in Preparation 15.

Preparation 24 (R$^3$=C$_6$H$_5$)
(E)-2-Phenyl-5-(3,5-di-tert-butyl-4-hydroxy)benzylidene-1, 2-isothiazolidine-1,1-dioxide (Ij)

According to a similar method to that of Preparation 15, an aldol reaction was carried out using compound 6a (2.47 g, 8.88 mmol) and N-phenyl-1,2-isothiazolidine-1,1-dioxide 4j (2.19 g, 11.10 mmol) to give 3.184 g (75%) of adduct 7j. The adduct 7j (3.184 g, 6.69 mmol) was treated in toluene (100 ml) with p-toluenesulfonic acid hydrate (750 mg) to give the desired compound Ij (667 mg, 24%). M.p.= 195–196° C. IR (KBr)cm$^{-1}$: 3560, 3520, 2960, 1636, 1593, 1492, 1430, 1295, 1268, 1105, 1092. NMR (CDCl$_3$) δ: 1.47 (18H, s, 2×But), 3.31 (2H, dt, J=2.6, 6.6 Hz, CH$_2$), 3.80 (2H, t, J=6.6 Hz, CH$_2$), 5.54 (1H, s, OH), 7.17–7.26 (2H, m, aromatic-H, CH), 7.29 (2H, s, 2×aromatic-H), 7.38–7.42 (4H, m, 4×aromatic-H). Elementary analysis (C$_{24}$H$_{31}$NO$_3$S×0.1H$_2$O) Calcd: C, 69.39; H, 7.61; N, 3.37; S, 7.72. Found: C, 69.27; H, 7.60; N, 3.39; S, 7.61.

Preparation 25 (R$^3$=4-chlorophenyl)
(E)-2-(4-Chlorophenyl)-5-(3,5-di-tert-butyl-4-hydroxy) benzylidene-1,2-isothiazolidine-1,1-dioxide (Ik)

According to a similar method to that of Preparation 15, an aldol reaction was carried out using compound 6a (2.25 g, 8.09 mmol) and N-(4-chlorophenyl)-1,2-isothiazolidine-1,1-dioxide 4k (2.34 g, 10.1 mmol) to give 2.54 g (62%) of adduct 7k. The adduct 7k (2.53 g, 4.96 mmol) was treated in toluene (70 ml) with p-toluenesulfonic acid hydrate (250 mg) to give the desired compound Ik (859 mg, 39%). M.p.=245–246° C. IR (KBr)cm$^{-1}$: 3560, 2960, 1644, 1592, 1491, 1430, 1280, 1105, 1090. NMR (CDCl$_3$) δ: 1.46 (18H, s, 2×But), 3.30 (2H, dt, J=2.6, 6.6 Hz, CH$_2$), 3.76 (2H, t, J=6.6 Hz, CH$_2$), 5.55 (1H, s, OH), 7.28 (2H, s, 2×aromatic-H), 7.26–7.40 (5H, m, 4×aromatic-H, CH). Elementary analysis (C$_{24}$H$_{30}$NO$_3$SCl) Calcd: C, 64.34; H, 6.75; N, 3.13; S, 7.16; Cl, 7.91. Found: C, 64.59; H, 6.78; N, 3.28; S, 7.17; Cl, 7.87.

Preparation 26 (R$^3$=2-pyridyl)
(E)-2-(2-Pyridyl)-5-(3,5-di-tert-butyl-4-hydroxy benzylidene-1,2-isothiazolidine-1,1-dioxide (Il)

According to a similar method to that of Preparation 15, an aldol reaction was carried out using compound 6a (208 mg, 0.75 mmol) and N-(2-pyridyl)-1,2-isothiazolidine-1,1-dioxide 4l (149 mg, 0.75 mmol) to give 233 mg (65%) of adduct 7l. The adduct 7l (231 mg, 0.485 mmol) was treated in toluene (5 ml) with p-toluenesulfonic acid hydrate (60 mg) to give the desired compound Il (96 mg, 48%). M.p.= 177–179° C. IR (KBr)cm$^{-1}$: 3570, 2960, 1646, 1600, 1587, 1472, 1431, 1300, 1105, 1085. NMR (CDCl$_3$) δ: 1.47 (18H, s, 2×But), 3.31 (2H, dt, J=2.4, 6.8 Hz, CH$_2$), 4.08 (2H, t, J=6.8 Hz, CH$_2$), 5.55 (1H, s, OH), 6.99–7.05 (1H, m, CH), 7.28 (2H, s, 2×aromatic-H), 7.38 (1H, t, J=2.4 Hz, Py-H), 7.55–7.74 (2H, m, 2×Py-H), 8.33–8.36 (1H, m, Py-H). Elementary analysis (C$_{23}$H$_{30}$N$_2$O$_3$S) Calcd: C, 66.63; H, 7.29; N, 6.76; S, 7.73. Found: C, 66.31; H, 7.30; N, 6.72; S, 7.66.

Preparation 27 (R$^3$=3-pyridyl)
(E)-2-(3-Pyridyl)-5-(3,5-di-tert-butyl-4-hydroxy) benzylidene-1,2-isothiazolidine-1,1-dioxide (Im)

According to a similar method to that of Preparation 15, an aldol reaction was carried out using compound 6a (1.474 g, 5.30 mmol) and N-(3-pyridyl)-1,2-isothiazolidine-1,1-dioxide 4m (1.051 g, 5.30 mmol) to give 1.522 g (60%) of adduct 7m. The adduct 7m (1.522 g, 3.19 mmol) was treated in toluene (40 ml) with p-toluenesulfonic acid hydrate (400 mg) to give 358 mg (27%) of the desired compound Im. M.p.=207–209° C. IR (KBr)cm$^{-1}$: 3625, 3040, 2960, 1640, 1590, 1480, 1431, 1305, 1152. NMR (CDCl$_3$) δ: 1.47 (18H, s, 2×But), 3.36 (2H, dt, J=2.4, 6.4 Hz, CH$_2$), 3.84 (2H, t, J=6.4 Hz, CH$_2$), 5.59 (1H, s, OH), 7.29 (2H, s, 2×aromatic-H), 7.29–7.40 (2H, m, CH, Py-H), 7.84–7.93 (1H, m, Py-H), 8.37–8.64 (2H, m, 2×Py-H). Elementary analysis (C$_{23}$H$_{30}$N$_2$O$_3$S) Calcd: C, 66.63; H, 7.29; N, 6.76; S, 7.73. Found: C, 66.31; H, 7.27; N, 6.69; S, 7.47.

Preparation 28 (R$^3$=4-pyridyl)
(E)-2-(4-Pyridyl)-5-(3,5-di-tert-butyl-4-hydroxy) benzylidene-1,2-isothiazolidine-1,1-dioxide (In)

According to a similar method to that of Preparation 15, an aldol reaction was carried out using compound 6a (2.59 g, 9.36 mmol) and N-(4-pyridyl)-1,2-isothiazolidine-1,1- dioxide 4n (2.05 g, 10.4 mmol) to give 2.721 g (61%) of adduct 7n. The adduct 7n (1.65 g, 3.46 mmol) was treated in toluene (80 ml) with p-toluenesulfonic acid hydrate (433 mg) to give 658 mg (46%) of the desired compound In. M.p.=213–214.5° C. IR (kBr)cm$^{-1}$: 3400, 2955, 1643, 1591, 1502, 1437, 1316, 1153. NMR (CDCl$_3$) δ: 1.47 (18H, s, 2×But), 3.37 (2H, dt, J=2.2, 6.8 Hz, CH$_2$), 3.82 (2H, t, J=6.8 Hz, CH$_2$), 5.61 (1H, s, OH), 7.21–7.25 (4H, m, 2×aromatic-H, 2×Py-H), 7.42 (1H, t, J=2.2 Hz, CH), 8.50–8.58 (2H, m, 2×Py-H). Elementary analysis (C$_{23}$H$_{30}$N$_2$O$_3$S) Calcd: C, 66.63; H, 7.29; N, 6.76; S, 7.73. Found: C, 66.46; H, 7.18; N; 6.66; S, 7.49.

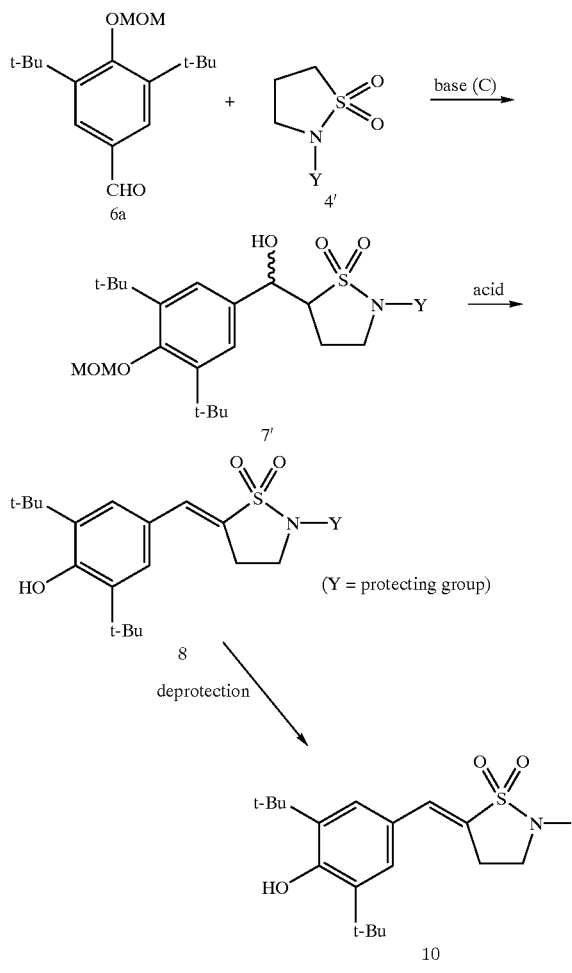

Preparation 29 (R$^3$=H) (Y=CO$_2$C(CH$_3$)$_3$)
(E)-5-(3,5-Di-tert-butyl-4-hydroxy)benzylidene-1,2-isothiazolidine-1,1-dioxide (10)

According to a similar method to that of Preparation 15, an aldol reaction was carried out using compound 6a and N-(tert-butoxycarbonyl)-1,2-isothiazolidine-1,1-dioxide 4o, which had been prepared from starting materials, 3-chloropropylsulfonyl chloride and tert-butyl carbonate, in accordance with the method of reaction scheme I, to give a crude adduct 7o. To a solution of the crude adduct 7o in toluene was added p-toluenesulfonic acid hydrate and the resultant mixture was heated to reflux for 45 minutes and then subjected to column chromatography on silica gel. From the fraction eluted with a mixture of n-hexane/ethyl acetate (2:1), the desired compound 10 (yield 8.5%) was obtained. M.p.=233–234° C. IR (CHCl$_3$)cm$^{-1}$: 3618, 2952, 1435, 1366, 1311, 1240, 1155, 1070. NMR (CDCl$_3$) δ: 1.45 (18H, s, 2×But), 3.18 (2H, dt, J=2.6, 6.8 Hz, CH$_2$), 3.42–3.60 (2H, m, CH$_2$), 4.05–4.25 (1H, broad, NH), 5.52 (1H, s, OH), 7.22–7.27 (3H, m, 2×aromatic-H, CH). Elementary analysis (C$_{18}$H$_{27}$NO$_3$S×0.35H$_2$O) Calcd: C, 62.89; H, 8.12; N, 4.07; S, 9.38. Found: C, 63.10; H, 7.90; N, 4.17; S, 9.11.

Preparation 30 (R$^3$=H) (Y=4-methoxybenzyl)
(Z)-5-(3,5-Di-tert-butyl-4-hydroxy)benzylidene-1,2-isothiazolidine-1,1-dioxide (10)

To a solution of the adduct 7h (13.16 g, 25.3 mmol) of the aldol reaction, which was obtained in a manner as described in Preparation 22, in toluene (150 ml) was added p-toluenesulfonic acid hydrate (1.3 g). The resultant mixture was heated to reflux for 30 minutes and filtered through a small amount of silica gel. The solvent was removed in vacuo to give a mixture (8.83 g) of crude (E)- and (Z)-2-(4-methoxybenzyl)-5-(3,5-di-tert-butyl-4-hydroxy)benzylidene-1,2-isothiazolidine-1,1-dioxides. To a solution of the mixture in methylene chloride (150 ml) was added titanium tetrachloride (4.1 ml). The resultant mixture was stirred for 30 minutes at 0° C. and then subjected to column chromatography on silica gel. From the fraction eluted with a mixture of n-hexane/ethyl acetate (1:1), compounds 10 (3.35 g, 41%) was obtained. Compound 10 was identical with the sample obtained in Preparation 29.

Preparation 31 (R$^3$=H)(Y=3,4-dimethoxybenzyl)
To a solution of the adduct 7i (4.0 g, 7.3 mmol) of the aldol reaction obtained in Preparation 9 in xylene (50 ml) were added an equimolar amount of each of 2,6-di-tert-butylphenol, anisole and p-toluenesulfonic acid hydrate. The resultant mixture was heated to reflux for 45 minutes, and the reaction product was subjected to column chromatography on silica gel to give compounds 10 (580 mg, 24%). Compound 10 was identical with the samples obtained in Preparations 29 and 30, respectively.

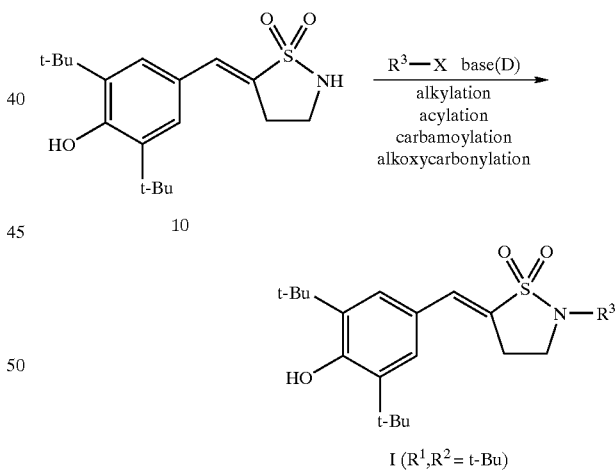

Preparation 32 (R$^3$=CH$_2$CO$_2$C$_2$H$_5$)
(E)-2-Ethoxycarbonylmethyl-5-(3,5-di-tert-butyl-4-hydroxy)benzylidene-1,2-isothiazolidine-1,1-dioxide (Ip)

(E)-5-(3,5-Di-tert-butyl-4-hydroxy)benzylidene1,2-isothiazolidine-1,1-dioxide 10 (500 mg, 1.48 mmol), ethyl iodoacetate (240 μl, 2 mmol), an aqueous solution of 2N sodium hydroxide (1.5 ml, 3 mmol) and a small amount of N-benzyltrimethylammonium chloride were sequentially added to a mixture of chloroform (20 ml) and water (10 ml). The resultant mixture was stirred for 24 hours at room temperature and then treated in a conventional manner. The product was purified by column chromatography on silica gel to give 300 mg (49%) of the desired compound Ip. IR (CHCl$_3$)cm$^{-1}$: 3620, 2956, 1747, 1435, 1298, 1229, 1160. NMR (CDCl$_3$) δ: 1.29 (3H, t, J=7.2 Hz, CH$_3$), 1.45 (18H, s, 2×But), 3.19 (2H, dt, J=2.6, 6.6 Hz, CH$_2$), 3.51 (2H, t, J=6.6 Hz, CH$_2$), 3.87 (2H, s, CH$_2$CO), 4.23 (2H, q, J=7.2 Hz, CH$_2$), 5.52 (1H, s, OH), 7.22–7.30 (3H, m, 2×aromatic-H, CH).

Preparation 33 (R$^3$=CH$_2$COOH)
(E)-2-Carboxymethyl-5-(3,5-di-tert-butyl-4-hydroxy)benzylidene-1,2-isothiazolidine-1,1-dioxide (Iq)

Compound Ip (610 mg, 1.44 mmol) as obtained in a similar manner as described in Preparation 32 and an aqueous solution of 2N sodium hydroxide (1.5 ml) were added to a mixture of THF (10 ml) and methanol (4 ml). The resultant mixture was stirred at 0° C. for 30 minutes. After the addition of ethyl acetate (50 ml), the reaction mixture was washed with an aqueous solution of 1N hydrochloric acid (20 ml), then a saturated brine (20 ml), and dried over anhydrous sodium sulfate. The solvent was removed in vacuo to give 445 mg (78%) of the desired compound Iq. M.p=175–178° C. IR (CHCl$_3$)cm$^{-1}$: 3620, 2954, 1735, 1435, 1297, 1240, 1149. NMR (CDCl$_3$) δ: 1.45 (18H, s, 2×But), 3.20 (2H, dt, J=2.6, 6.6 Hz, CH$_2$), 3.51 (2H, t, J=6.6 Hz, CH$_2$), 3.95 (2H, s, CH$_2$CO), 5.54 (1H, s, OH), 7.25 (2H, s, 2×aromatic-H). Elementary analysis (C$_{20}$H$_{29}$NO$_5$S) Calcd: C, 60.46; H, 7.41; N, 3.53; S, 8.07. Found: C, 60.34; H, 7.40; N, 3.56; S, 8.04.

Preparation 34 (R$^3$=CH$_2$CH$_2$OH)
(E)-2-(2-Hydroxyethyl)-5-(3,5-di-tert-butyl-4-hydroxy)benzylidene-1,2-isothiazolidine-1.1-dioxide (Ir)

Compound 10 (675 mg, 2 mmol), 2-iodoethanol (624 μl, 8 mmol), an aqueous solution of 2N sodium hydroxide (2 ml) and a small amount of N-benzyltrimethylammonium chloride were added to a mixture of methylene chloride (20 ml) and water (10 ml). The resultant mixture was heated to reflux for 3 days and treated in a conventional manner and the product was subjected to column chromatography on silica gel. From the fraction eluted with a mixture of n-hexane/ethyl acetate (7:3), 190 mg (25%) of the desired compound Ir was obtained. M.p.=156–157° C. IR (CHCl$_3$) cm$^{-1}$: 3620, 2950, 1434, 1290, 1240, 1151, 1066. NMR (CDCl$_3$) δ: 1.45 (18H, s, 2×But), 3.16 (2H, dt, J=2.4, 6.5 Hz, CH$_2$), 3.30 (2H, m, CH$_2$), 3.41 (2H, t, J=6.5 Hz, CH$_2$), 3.87 (2H, t, J=5.2 Hz), 5.53 (1H, s, OH), 7.23–7.29 (3H, m, 2×aromatic-H, CH). Elementary analysis (C$_{20}$H$_{31}$NO$_4$S) Calcd: C, 62.96; H, 8.19; N, 3.67; S, 8.40. Found: C, 62.72; H, 8.27; N, 3.69; S, 8.21.

Preparation 35 (R$^3$=CH$_2$CH$_2$N(CH$_3$)$_2$)
(E)-2-(2-Dimethylamino) ethyl)-5-(3,5-di-tert-butyl-4-hydroxy)benzylidene-1,2-isothiazolidine-1,1-dioxide (Is)

Compound 10 (843 mg, 2.5 mmol), N,N-dimethyl-2-bromoethylamine (750 mg, 5 mmol), an aqueous solution of 2N sodium hydroxide (3 ml, 6 mmol) and a small amount of N-benzyltrimethylammonium chloride were added to a mixture of chloroform (30 ml) and water (10 ml). The resultant mixture was stirred for 2 hours under ice-cooling. The chloroform layer was washed with water (20 ml×2) and dried over anhydrous sodium sulfate. Chloroform was removed in vacuo to give 950 mg (93%) of the desired compound as a crystalline residue. M.p.=160–165° C. IR (CHCl$_3$)cm$^{-1}$: 3620, 2956, 1435, 1290, 1148. NMR (CDCl$_3$) δ: 1.45 (18H, s, 2×But), 2.29 (6H, s, N(CH$_3$)$_2$), 2.60 (2H, t, J=6.6 Hz, CH$_2$), 3.12 (2H, dt, J=2.2, 6.6 Hz, CH$_2$), 3.20 (2H, t, J=6.6 Hz, CH$_2$), 3.38 (2H, t, J=6.6 Hz, CH$_2$), 5.51 (1H, s, OH), 7.21–7.28 (3H, m, 2×aromatic-H, CH). Elementary analysis (C$_{22}$H$_{36}$N$_2$O$_3$S×0.2CH$_2$Cl$_2$) Calcd: C, 62.65; H, 8.62; N, 6.58; S, 7.53; Cl, 3.33. Found: C, 62.32; H, 8.60; N, 6.71; S, 7.56; Cl, 3.24.

Preparation 36 (R$^3$=COCH$_3$)
(E)-2-Acetyl-5-(3,5-di-tert-butyl-4-hydroxy)benzylidene-1,2-isothiazolidine-1,1-dioxide (It)

To a solution of compound 10 (585 mg, 1.74 mmol) in pyridine (10 ml), a small amount of 4-N,N-dimethylaminopyridine was added, and acetic anhydride (6 ml) was dropwise added under ice-cooling. The resultant mixture was stirred for 1 hour at room temperature. The mixture was concentrated under reduced pressure, and the residue was dissolved in ethyl acetate and the solution was filtered through a small amount of silica gel. The solvent was removed in vacuo to give 360 mg (55%) of the desired compound as a crystal-like residue. M.p.=177–179° C. IR (CHCl$_3$)cm$^{-1}$: 3618, 2958, 1695, 1435, 1379, 1297, 1153, 1117. NMR (CDCl$_3$) δ: 1.46 (18H, s, 2×But), 2.53 (3H, s, COCH$_3$), 3.20 (2H, dt, J=2.2, 7.0 Hz, CH$_2$), 3.86 (2H, t, J=7.0 Hz, CH$_2$), 5.60 (1H, s, OH), 7.52 (2H, s, 2×aromatic-H), 7.39 (1H, t, J=2.2 Hz, CH). Elementary analysis (C$_{20}$H$_{29}$NO$_4$S) Calcd: C, 63.30; H, 7.70; N, 3.69; S, 8.45. Found: C, 63.27; H, 7.83; N, 3.64; S, 8.22.

Preparation 37 ((R$^3$=N-methyl-N-methoxy)carbamoyl)
(E)-2-(N-Methyl-N-methoxy)carbamoyl-5-(3,5-di-tert-butyl-4-hydroxy)benzylidene-1,2-isothiazolidine-1,1-dioxide (Iu)

Compound 10 (450 mg, 1.33 mmol) and N-methyl-N-methoxy-O-phenyl carbamate (300 mg, 1.66 mmol) were dissolved in a mixture of THF (10 ml) and HMPA (10 ml). To the solution was dropwise added absolution of lithium hexamethyldisilazane (LiHMDS) in THF (1 M, 3.2 ml) with stirring and cooling to –40° C. The reaction mixture was warmed to room temperature and poured into an aqueous solution of 1N hydrochloric acid (20 ml). The mixture was extracted with ethyl acetate (30 ml), and then the ethyl acetate layer was washed with water (30 ml) and a saturated brine (30 ml), dried over anhydrous sodium sulfate. The solvent was removed under reduced pressure, and the residue was subjected to column chromatography on silica gel. From the fraction eluted with a mixture of n-hexane/ethyl acetate (7:3), the desired compound Iu (230 mg, 41%) was obtained. IR (CHCl$_3$)cm$^{-1}$: 3620, 2958, 1673, 1435, 1388, 1330, 1240, 1207, 1155, 1092. NMR (CDCl$_3$) δ: 1.45 (18H, s, 2×But), 3.21 (2H, dt, J=2.2, 6.8 Hz, CH$_2$), 3.31 (3H, s, NCH$_3$), 3.78 (3H, s, OCH$_3$), 3.89 (2H, t, J=6.8 Hz), 5.54 (1H, s, OH), 7.23 (2H, s, 2×aromatic-H), 7.31 (1H, t, J=2.2 Hz, CH).

Preparation 38 ((R$^3$=N-benzyloxy-N-methoxymethyl)carbamoyl)
(E)-2-(N-Benzyloxyl-N-methoxymethyl)carbamoyl-5-(3,5-di-tert-butyl-4-hydroxy)benzylidene-1,2-isothiazolidine-1,1-dioxide (Iv)

Compound 10 (424 mg, 1.26 mmol) and N-benzyloxy-N-methoxymethyl-O-phenyl carbamate (722 mg, 2.52 mmol) were treated in a mixture of THF (90 ml) and HMPA (30 ml) with a solution of LIHMDS in THF (1 M, 4.0 ml), in a manner as described in Preparation 37. The reaction product was subjected to column chromatography on silica gel. From the fraction eluted with a mixture of n-hexane/ethyl acetate (3:1), the desired compound Iv (600 mg, 90%) was obtained. NMR (CDCl$_3$) δ: 1.45 (18H, s, 2×But), 3.18 (2H, dt, J=2.0, 6.8 Hz, CH$_2$), 3.45 (3H, s, OCH$_3$), 3.79 (2H, t, J=6.8 Hz, CH$_2$), 4.94 (2H, s, OCH$_2$), 5.02 (2H, s, OCH$_2$), 5.54 (1H, s, OH), 7.22 (2H, s, 2×aromatic-H), 7.30 (1H, t, J=2.0 Hz, CH), 7.30–7.55 (5H, m, 5×aromatic-H).

Preparation 39 (R$^3$=CONHOH)
(E)-2-(Hydroxycarbamoyl)-5-(3,5-di-tert-butyl-4-hydroxy)benzylidene-1.2-isothiazolidine-1,1-dioxide (Iw)

To a solution of compound Iv (600 mg, 1.13 mmol) obtained in Preparation 38 in methylene chloride (8 ml) was added titanium tetrachloride (500 μl, 4.56 mmol) under ice-cooling, and the resultant mixture was stirred for 1.5 hours. After an aqueous solution of 2N hydrochloric acid (10 ml) was added, the reaction mixture was stirred for 30 minutes at room temperature and then extracted with methylene chloride (20 ml). The organic layer was washed with a saturated brine (20 ml), dried over anhydrous sodium sulfate. The solvent was removed under reduced pressure, and the residue was subjected to column chromatography on silica gel. From the fraction eluted with a mixture of n-hexane/ethyl acetate (1:1), the desired compound Iw (150 mg, 33%) was obtained. IR (CHCl$_3$)cm$^{-1}$: 3618, 2956, 1707, 1434, 1320, 1151, 1100. NMR (CDCl$_3$) δ: 1.45 (18H, s, 2×But), 3.23 (2H, dt, J=2.2, 7.0 Hz, CH$_2$), 3.94 (2H, t, J=7.0 Hz, CH$_2$), 5.61 (1H, s, OH), 6.85–6.95 (1H, broad, OH), 7.24 (2H, s, 2×aromatic-H), 7.30 (1H, t, J=2.2 Hz, CH), 8.61 (1H, s, NH).

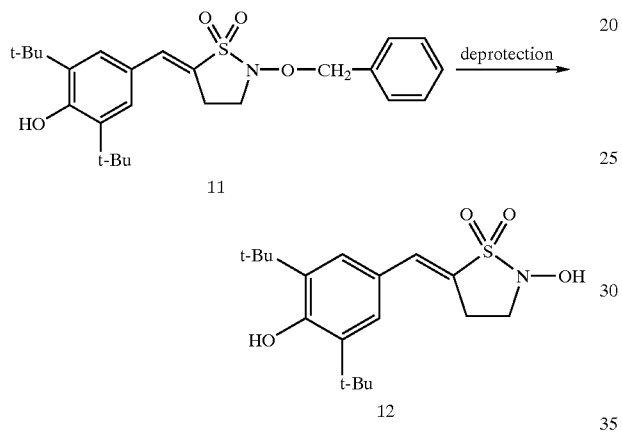

Preparation 40
(E)-2-Hydroxy-5-(3,5-di-tert-butyl-4-hydroxy)benzylidene-1,2-isothiazolidine-1,1-dioxide (12)

According to a similar method to that of Preparation 15, an aldol reaction was carried out using compound 6a and N-benzyloxy-1,2-isothiazolidine-1,1-dioxide. The adduct obtained by the aldol reaction was then treated with p-toluenesulfonic acid hydrate to give crude 2-benzyloxy-5-(3,5-di-tert-butyl-4-hydroxy)benzylidene-1,2-isothiazolidine-1,1-dioxide 11. To a solution of the crude dioxide (4.44 g, 10 mmol) in methylene chloride (80 ml) was dropwise added titanium tetrachloride (4.4 ml, 40 mmol) with stirring and ice-cooling, and the mixture was stirred for another 2 hours at the same temperature. An aqueous solution of 1N hydrochloric acid (50 ml) was added to the reaction mixture. The methylene chloride layer was separated, washed sequentially with water (50 ml) and a saturated brine (50 ml), dried over anhydrous sodium sulfate. The solvent was removed under reduced pressure, and the residue was subjected to column chromatography on silica gel. From the fraction eluted with a mixture of n-hexane/ethyl acetate (3:1), the desired compound 12 (1.6 g, 45%) was obtained. M.p.=177–182° C. (decomp.). IR (KBr)cm$^{-1}$: 3560, 3430, 1425, 1330, 1240, 1155, 1130, 1115. NMR (CDCl$_3$) δ: 1.45 (18H, s, 2×But), 3.18 (2H, dt, J=2.6, 6.8 Hz, CH$_2$), 3.89 (2H, t, J=6.8 Hz, CH$_2$), 5.56 (1H, s, OH), 6.18–6.30 (1H, broad, OH), 7.26–7.35 (3H, m, 2×aromatic-H, CH). Elementary analysis (C$_{18}$H$_{27}$NO$_4$S) Calcd: C, 61.16; H, 7.70; N, 3.96; S, 9.07. Found: C, 60.86; H, 7.68; N, 3.93; S, 8.90.

Preparation 41
(E)-2-Isopropyl-5-(3,5-di-tert-butyl-4-hydroxy)benzylidene-1,2-isothiazolidine-1,1-dioxide (Ix)

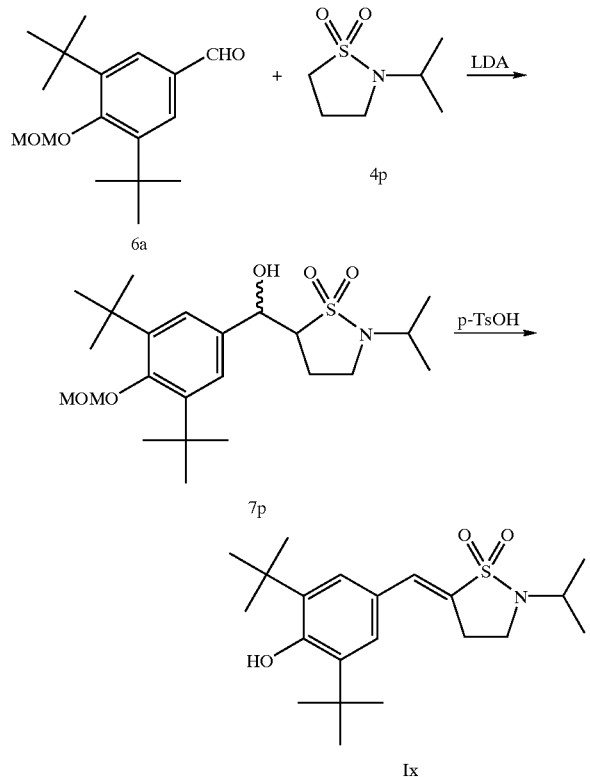

According to a similar method to that of Preparation 15, an aldol reaction was carried out using N-isopropyl-1,2-isothiazolidine-1,1-dioxide 4p (3.65 g, 22.4 mmol) and 3,5-di-tert-butyl-4-methoxymethoxybenzaldehyde 6a (5.28 g, 19.0 mmol) to give 6.27 g (74.7%) of adduct 7p as a white powder. To a solution of the adduct 7p (6.27 g) in toluene (120 ml) was added p-toluenesulfonic acid hydrate (600 mg). The mixture was heated to reflux for 30 minutes, cooled, washed twice with water (100 ml), dried over anhydrous sodium sulfate, and the solvent was removed under reduced pressure. The crystalline residue was recrystallized from methanol to give 2.16 g (30%) of the desired compound Ix as colorless columnar crystals. M.p.= 148–150° C. IR (KBr)cm$^{-1}$: 3550, 2960, 1645, 1600, 1432, 1273, 1173. NMR (CDCl$_3$) δ: 1.29 (6H, d, J=6.6 Hz, 2×CH$_3$), 1.45 (18H, s, 2×But), 3.07–3.14 (2H, m, CH$_2$), 3.29–3.35 (2H, m, CH$_2$), 3.94 (1H, sept, CH), 5.48 (1H, s, OH), 7.22 (1H, t, J=2.8 Hz, CH), 7.23 (2H, s, Ar—H). Elementary analysis (C$_{21}$H$_{33}$NO$_3$S) Calcd: C, 66.45; H, 8.76; N, 3.69; S, 8.45. Found: C, 66.37; H, 9.01; N, 3.67; S, 8.28.

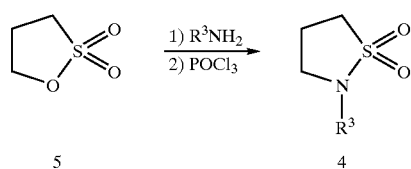

Preparation 42 (R$^3$=CH$_2$CH$_2$CH$_3$)
N-n-Propyl-1,2-isothiazolidine-1,1-dioxide (4e)

To γ-sultone (12.2 g, 0.1 mol) was added n-propylamine (5.9 g, 0.1 mmol) with stirring and ice-cooling. As the reaction proceeds, the contents solidified. To the solid product was added phosphorus oxychloride (10 ml). The reaction mixture was heated to reflux for 2 hours, and the remaining phosphorus oxychloride was removed under reduced pressure. After the addition of ether (100 ml) to the residue, insoluble substances were removed by filtration. The ether layer was dried over anhydrous sodium sulfate, and the solvent was removed in vacuo to give the desired compound 4e (15.2 g, 93%) as a colorless oil. This product was identical with the sample obtained in Preparation 5.

Preparation 43 ($R^3=CH_2CH(CH_3)_2$)

N-Isobutyl-1,2-isothiazolidine-1,1-dioxide (4c)

According to a similar method to that of Preparation 1, γ-sultone (12.2 g, 0.1 mol), isobutylamine (7.3 g, 0.1 mol) and phosphorus oxychloride (10 ml) were reacted to give the desired compound 4c (15.9 g, 90%). This product was identical with the sample obtained in Preparation 3.

Novel compounds of the present invention can be prepared according to the following Examples, and the processes for the production described therein per se are not to be construed as limiting the present invention. One example of the processes for the production of the novel compounds of the present invention is provided below.

EXAMPLES

Example 1

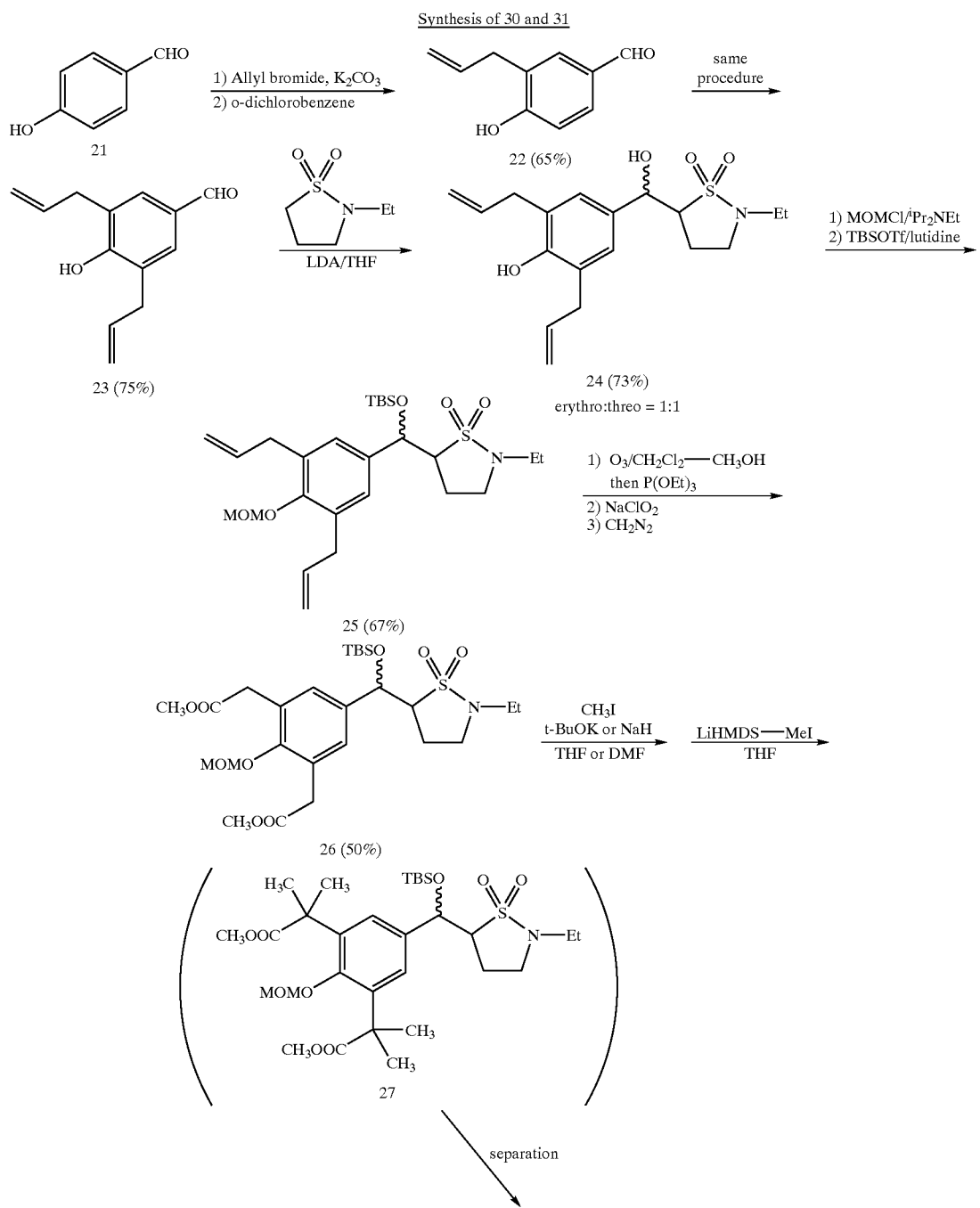

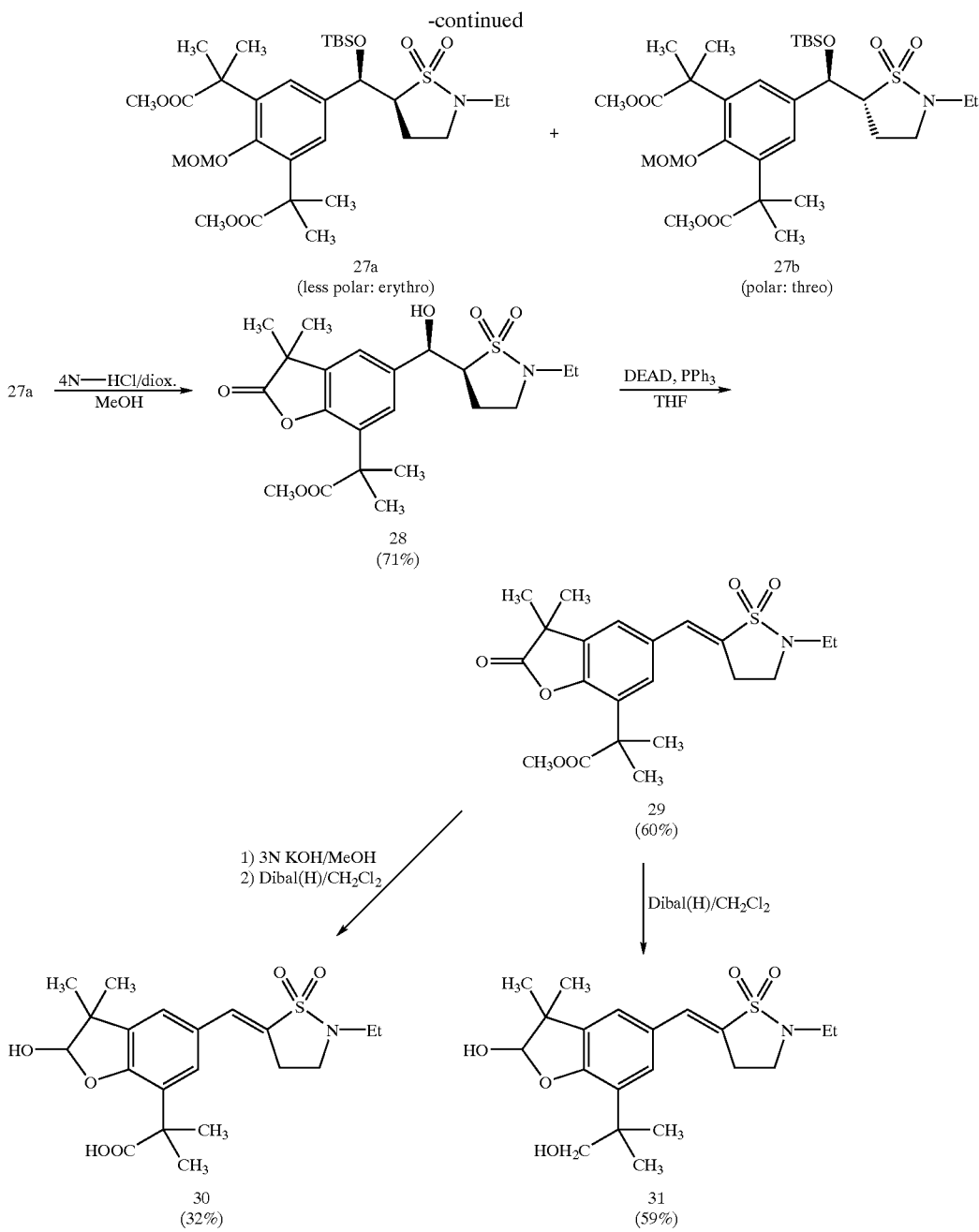

a. 3,5-Diallyl-4-hydroxybenzaldehyde (23)

The titled compound was synthesized according to the process described in the literature with a partial modification. See Claisen; Eisleb, Justus Liebigs Ann. Chem., 401, 108 (1913).

b. 2,6-Diallyl-4-((2-ethyl-1,1-dioxo-1,2-isothiazolidin-5-yl)hydroxy-methyl)phenol (24)

LDA (2.0 M solution in THF) (4.52 ml, 9.04 mmol) was dropwise and slowly added to a solution of 23 (850 mg, 4.20 mmol) and 2-ethyl-1,2-isothiazolidin-1,1-dioxide (752 mg, 5.04 mmol) in THF (15 ml), while maintaining the temperature below −45° C. The reaction mixture was warmed to 0° C. and stirred for another 1 hour. The mixture was added with diluted hydrochloric acid and extracted with ethyl acetate. The organic layer was washed with water and saturated brine, dried over anhydrous sodium sulfate, and the solvent was removed in vacuo. The residue was purified by column chromatography on silica gel to yield 1.083 g (73%) of 24 as a mixture of diastereomers: $^1$H NMR (CDCl$_3$) δ: 1.23–1.28 (3H, m), 1.75–2.06 (2H*½, m), 2.47–2.61 (2H*½, m), 2.95–3.53 (9H, m), 4.79–5.42 (6H, m), 5.90–6.08 (2H, m), 7.02 (2H, s).

c. 5-((tert-Butyl-dimethylsilanyloxy)-(3,3-diallyl-4-methoxymethoxyphenyl)-methyl)-2-ethyl-1,2-isothiazolidin 1,1-dioxide (25)

To a solution of 24 (1.789 g, 5.09 mmol) in dichloromethane (25 ml), under ice-cooling, diisopropylethylamine (4.43 ml, 25.45 mmol) and MOMCl (1.16 ml, 15.27 mmol) were dropwise added sequentially and slowly. After stirring at 0° C. for 1 hour and then at room temperature for 1 hour, the reaction mixture was added with diluted hydrochloric acid and extracted with chloroform. The organic layer was washed with water, saturated sodium bicarbonate and saturated brine. After drying over anhydrous sodium sulfate, the solvent was removed in vacuo. The residue was purified by column chromatography on silica gel to yield 1.470 g (73%) of an intermediate. This intermediate (805 mg, 2.035 mmol) was dissolved in dichloromethane (10 ml), 2,6-lutidine (0.71 ml, 6.105 mmol) and TBSOTf (0.70 ml, 3.05 mmol) were added to the solution under ice-cooling, and the mixture was stirred for 2 hours. The mixture was added with diluted hydrochloric acid and extracted with chloroform. The organic layer was washed with water, saturated sodium bicarbonate and saturated brine. After drying over anhydrous sodium sulfate, the solvent was removed in vacuo. The residue was purified by column chromatography on silica gel to yield 960 mg (92%) of 25.
$^1$H NMR (CDCl$_3$) δ: −0.25 (3H*½, s), −0.23 (3H*½, s), 0.08 (3H*½, s), 0.11 (3H*½, s), 0.83 (9H*½, s) 0.86 (9H*½, s), 1.20 (3H, t, J=7.2 Hz), 1.60–2.54 (2H, m), 2.91–3.52 (9H, m), 3.58 (3H*½, s), 3.59 (3H*½, s), 4.80–5.12 (7H, m), 5.85–6.04 (2H, m), 7.03 (2H*½, s), 7.06 (2H*½, s).

d. Methyl (5-((2-ethyl-1,1-dioxo-1,2-isothiazolidin-5-yl)-(tert-butyl-dimethylsilanyloxy)-methyl)-3-methoxycarbonylmethyl-2-methoxymethoxy-phenyl) acetate (26)

Ozone gas was passed through a solution of 25 (3.90 g, 7.65 mmol) in dichloromethane (100 ml) and methanol (20 ml) at −78° C. until the color of the solution turned to blue. To the reaction mixture, triethylphosphite (3.94 ml, 23 mmol) was added, and the mixture was slowly warmed to room temperature. The reaction mixture was concentrated, and the residue was added with t-butanol (40 ml), H$_2$O (10 ml), 2-methyl-2-butene (8.1 ml, 76.5 mmol) and NaH$_2$PO$_4$ (2.31 g, 15.3 mmol). NaClO$_2$ (3.50 g, 30.6 mmol) was then slowly added to the mixture at room temperature. After stirring overnight, the mixture was added with hydrochloric acid and extracted with chloroform. The organic layer was washed with saturated brine, dried and concentrated. The resultant residue was added with ethyl acetate, and excess amount of an ether solution of diazomethane was dropwise added to the mixture under ice-cooling. The reaction mixture was concentrated and purified by column chromatography on silica gel to yield 2.187 g (50%) of 26. $^1$H NMR (CDCl$_3$) δ: −0.23 (3H*½, s), −0.21 (3H*½, s), 0.09 (3H*½, s), 0.12 (3H*½, s), 0.84 (9H*½, s), 0.86 (9H*½, s), 1.19 (3H*½, t, J=7.2 Hz), 1.34 (3H*½, t, J=7.2 Hz), 1.62–2.58 (2H, m), 2.90–3.96 (14H, m), 4.85–5.13 (7H, m), 7.16 (2H*½, s), 7.21 (2H*½, s).

e. Methyl 2-(5-((2-ethyl-1,1-dioxo-1,2-isothiazolidin-5-yl)-(tert-butyl-dimethylsilanyloxy)-methyl)-3-(1-methoxycarbonyl-1-methyl-ethyl)-2-methoxymethoxy-phenyl)-2-methyl-propionate (27a and 27b)

A solution of 26 (4.54 g, 7.91 mmol) and MeI (3.95 ml, 63.3 mmol) in DMF (25 ml) was slowly and dropwise added to a suspension of NaH (60% in mineral oil, 1.26 g, 31.6 mmol) (n-hexane wash) in DMF (5 ml) under ice-cooling. After stirring overnight at room temperature, the reaction mixture was added with diluted hydrochloric acid and extracted with ethyl acetate. The organic layer was washed with water and saturated brine. After drying over anhydrous sodium sulfate, the solvent was removed in vacuo to obtain a residue (3.90 g). To this residue, THF (40 ml) was added, and LiHMDS (1.0 M in THF) (14.25 ml, 14.25 mmol) was dropwise added over 10 minutes under ice-cooling. After stirring for another 45 minutes, the mixture was added with MeI (3.24 ml, 51.8 mmol) and warmed to room temperature. After stirring for 1.5 hours at room temperature, the mixture was added with diluted hydrochloric acid and extracted with ethyl acetate. The organic layer was washed with water and saturated brine. After drying over anhydrous sodium sulfate, the solvent was removed in vacuo. The residue was purified by column chromatography on silica gel to yield 2.50 g (48%) of the titled compound as a mixture of diastereomers ((27a) less polar, 1.08 g, (27b) more polar 1.42 g).

$^1$H NMR (CDCl$_3$) δ (27a): −0.20 (3H, s), 0.11 (3H, s), 0.88 (9H, s), 1.22 (3H, t, J=7.2 Hz), 1.53 (6H, s), 1.55 (6H, s), 2.44–2.60 (2H, m), 2.92–3.40 (5H, m), 3.49 (3H, s), 3.64 (6H, s), 4.78 (2H, ABq, J=4.5, 6.6 Hz), 5.18 (1H, d, J=4.8 Hz), 7.28 (2H, s).
$^1$H NMR (CDCl$_3$) δ (27b): −0.23 (3H, s), 0.12 (3H, s), 0.82 (9H, s), 1.21 (3H, t, J=7.2 Hz), 1.53 (6H, s), 1.58 (6H, s), 1.70–1.89 (2H, m), 2.94–3.67 (14H, m), 4.77 (2H, s), 4.80–4.92 (1H, m), 7.23 (2H, s).

f. Methyl 2-(5-((2-ethyl-1,1-dioxo-1,2-isothiazolidin-5-yl)-hydroxy-methyl)-3,3-dimethyl-2-oxo-2,3-dihydro-benzofuran-7-yl)-2-methyl-propionate (28)

To a solution of 27a (416 mg, 066 mmol) in methanol (6 ml), 4N HCl/dioxane (6 ml) was added under ice-cooling, and the mixture was stirred for 2 hours at room temperature. After the reaction mixture was concentrated, the mixture was added with water and extracted with ethyl acetate. The organic layer was washed with water and saturated brine, dried, and concentrated. The residue was purified by column chromatography on silica gel to yield 207 mg (71%) of 28.
$^1$H NMR (CDCl$_3$) δ: 1.27 (3H, t, J=7.2 Hz), 1.49 (6H, s), 1.61 (6H, s), 1.97–2.10 (1H, m), 2.46–2.61 (1H, m), 3.02–3.80 (8H, m), 5.49 (1H, brs), 7.17 (1H, s), 7.20 (1H, s).

g. Methyl 2-(5-(2-ethyl-1,1-dioxo-1,2-isothiazolidin-5-ylidenemethyl)-3,3-dimethyl-2-oxo-2,3-dihydro-benzofuran-7-yl)-2-methyl-propionate (29)

To a solution of 28 (318 mg, 0.724 mmol) and Ph$_3$P (569 mg, 2.17 mmol) in THF (5 ml), DEAD (0.171 ml, 1.09 mmol) was slowly added under ice-cooling. After stirring for 1 hour, the reaction mixture was concentrated, and the residue was purified by column chromatography on silica gel to yield 183 mg (60%) of 29. Mp.116–120° C. (colorless powder). $^1$H NMR (CDCl$_3$) δ: 1.30 (3H, t, J=7.2 Hz), 1.51 (6H, s), 1.63 (6H, s), 3.10–3.22 (4H, m), 3.31 (2H, t, J=6.3 Hz), 7.15 (1H, d, J=1.8 Hz), 7.26–7.29 (2H, m).

h. 2-(5-(2-Ethyl-1,1-dioxo-1,2-isothiazolidin-5-ylidenemethyl)-2-hydroxy-3,3-dimethyl-2,3-dihydro-benzofuran-7-yl)-2-methyl-propionic acid (30)

2N KOH (1.5 ml) was added to a solution of 29 (19 mg, 0.0364 mmol) in methanol (2 ml), and the mixture was allowed to stand overnight at room temperature. The reaction mixture was concentrated, acidified with diluted hydrochloric acid, and extracted with ethyl acetate. The organic layer was washed with saturated brine, and after dryness, the solvent was removed in vacuo. The residue was added with dichloromethane (1 ml), cooled to −78° C., and slowly and dropwise added with DIBAL (0.93 M in n-hexane) (0.31 ml, 0.182 mmol). After 5 minutes, a saturated aqueous ammonium chloride solution was added to quench the reaction, diluted hydrochloric acid was added, and the mixture was extracted with ethyl acetate. The organic layer was washed with saturated brine, dried, and concentrated. The residue was purified by preparative TLC to yield 5.9 mg (32%) of 30. $^1$H NMR (d$_6$-aceton) δ: 1.23 (3H, t, J=7.3 Hz), 1.29 (6H, br), 1.57 (6H, s), 3.06 (2H, q, J=7.3 Hz), 3.19 (2H, td, J=6.5, 2.6 Hz), 3.31 (2H, t, J=6.5 Hz), 5.66 (1H, s), 6.71 (1H, br), 7.12 (1H, t, J=2.6 Hz), 7.27 (1H, d, J=1.6 Hz), 7.34 (1H, d, J=1.6 Hz).

i. 5-(2-Ethyl-1,1-dioxo-1,2-isothiazolidin-5-ylidenemethyl)-7-(2-hydroxy-1,1-dimethyl-ethyl)-3,3-dimethyl-2,3-dihydro-benzofuran-2-ol (31) To a solution of 29 (56 mg, 0.133 mmol) in hexane (1 ml) and dichloromethane (1 ml) at −78° C., DIBAL (0.93 M) (0.64 ml, 0.595 mmol) was slowly added. The mixture was stirred for another 1 hour under the same conditions. The reaction mixture was added with diluted hydrochloric acid, warmed to room temperature, and stirred for another 15 minutes at room temperature. The resultant product was extracted with ethyl acetate, washed with water, saturated sodium bicarbonate, and saturated brine, dried, and concentrated. The residue was purified by column chromatography over silica gel to yield 31 mg (59%) of 31 as amorphous solid. Mp.78–82° C. $^1$H NMR (d$_6$-aceton) δ: 1.23 (3H, t, J=7.3 Hz), 1.26 (3H, brs), 1.34 (3H, brs), 1.36 (6H, s), 3.05 (2H, q, J=7.3 Hz), 3.19 (2H, m), 3.31 (2H, t, J=6.4 Hz), 3.59 (2H, t, J=5.6 Hz), 3.76 (2H, m), 5.66 (1H, s), 6.27 (1H, br), 7.11 (1H, t, J=2.7 Hz), 7.26 (1H, d, J=1.8 Hz), 7.36 (1H, d, J=1.8 Hz).

Example 2

Synthesis of 34

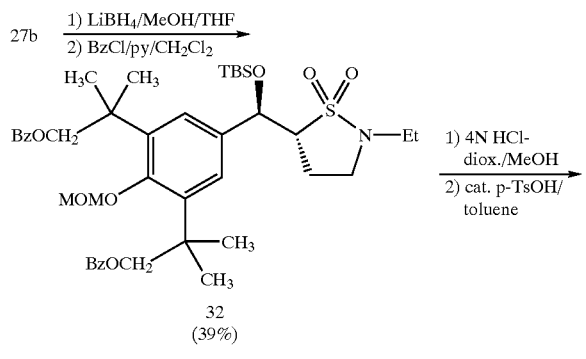

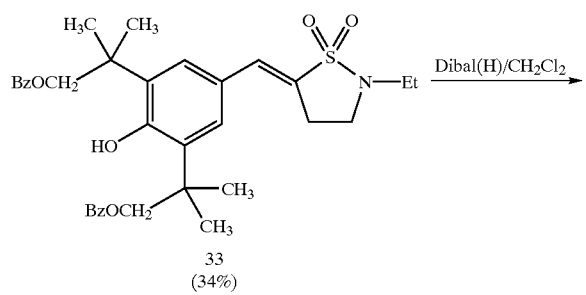

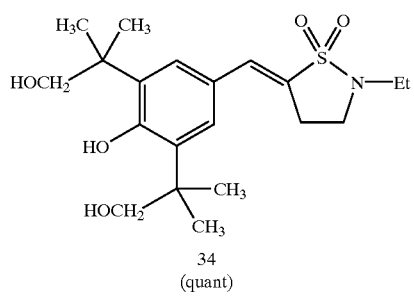

a. Benzoic-acid 2-(3-(2-benzoyloxy-1,1-dimethyl-ethyl)-5-((tert-butyl-dimethyl-silanyloxy)-(2-ethyl-1,1-dioxo-1,2-isothiazolidin-5-yl)-methyl)-2-methoxymethoxy-phenyl)-2-methyl-propyl Ester (32)

To a solution of 27b (529 mg, 0.84 mmol) in THF (8 ml), LiBH$_4$ (146 mg, 6.72 mmol) was added, and the mixture was refluxed for 5 hours. The reaction mixture was added with diluted hydrochloric acid and extracted with ethyl acetate. The organic layer was dried and purified by column chromatography on silica gel to yield 309 mg of diol. This diol (141 mg, 0.246 mmol) was benzoylated according to a conventional method to give 145 mg (39% for 2 steps) of 32. $^1$H NMR (CDCl$_3$) δ: –0.27 (3H, s), 0.10 (3H, s), 0.82 (9H, s), 1.46 (3H, t, J=7.2 Hz), 1.49 (12H, s), 2.60–3.32 (7H, m), 3.64 (3H, s), 4.62 (4H, ABq, J=11, 25 Hz), 4.81 (1H, d, J=9.3 Hz), 4.95 (2H, s), 7.26–7.87 (12H, m).

b. 4-(2-Ethyl-1,1-dioxo-1,2-isothiazolidin-5-ylidenemethyl)-2,6-bis-(2-benzoyloxy-1,1,dimethyl-ethyl)-phenol (33)

To a solution of 32 (45 mg, 0.0575 mmol) in methanol (1 ml), 4N HCl/dioxane (1 ml) was added under ice-cooling, and the mixture was warmed to room temperature and stirred for 2 hours. The mixture was treated in the manner as described above, and benzene (1 ml) and catalytic amount of p-TsOH were added to the residue, and the mixture was refluxed for 3 hours. The reaction mixture was added with water and extracted with ethyl acetate. The organic layer was washed with saturated brine, dried, and concentrated. The residue was purified by preparative TLC to yield 12 mg (34%) of 33. $^1$H NMR (CDCl$_3$) δ: 1.27 (3H, t, J=7.5 Hz), 1.54 (12H, s), 3.02 (2H, td, J=7.2, 2.7 Hz), 3.14 (2H, q, J=7.5 Hz), 3.18 (2H, t, J=7.2 Hz), 4.60 (4H, s), 7.24 (1H, t, J=2.7 Hz), 7.31 (2H, s), 7.38–7.93 (10H, m).

c. 4-(2-Ethyl-1,1-dioxo-1,2-isothiazolidin-5-ylidenemethyl)-2,6-bis-(2-hydroxy-1,1,dimethyl-ethyl)-phenol (34)

A solution of 33 (12 mg, 0.0198 mmol) in dichloromethane (1 ml) was cooled to –78° C., and DIBAL (0.93 M) (0.107 ml, 0.099 mmol) was slowly added. After 5 minutes, the mixture was added with diluted hydrochloric acid, warmed to room temperature and extracted with ethyl acetate. The organic layer was washed with water and saturated brine, dried, and the solvent was removed in vacuo. The residue was purified by preparative TLC to give 8.1 mg (quant) of 34. $^1$H NMR (d$_6$-aceton) δ: 1.23 (3H, t, J=7.3 HJz), 1.42 (12H, s), 3.04 (2H, q, J=7.5 Hz), 3.18 (2H, td, J=6.6, 2.6 Hz), 3.31 (2H, t, J=6.6 Hz), 3.82 (4H, s), 6.99 (1H, brs), 7.08 (1H, t, J=2.6 Hz), 7.39 (2H, s).

Example 3

Synthesis of 41

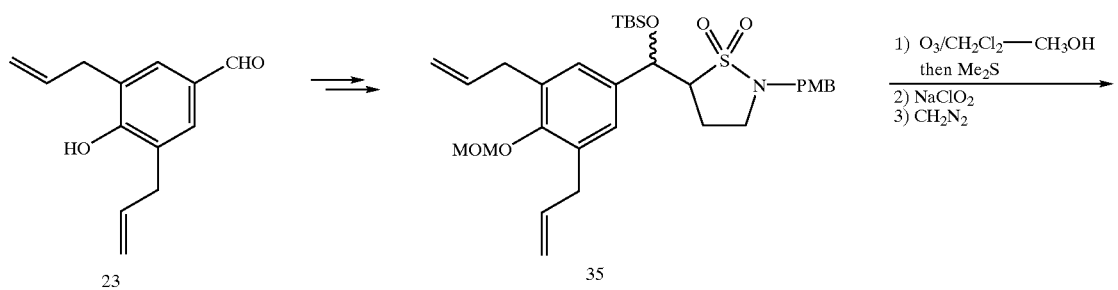

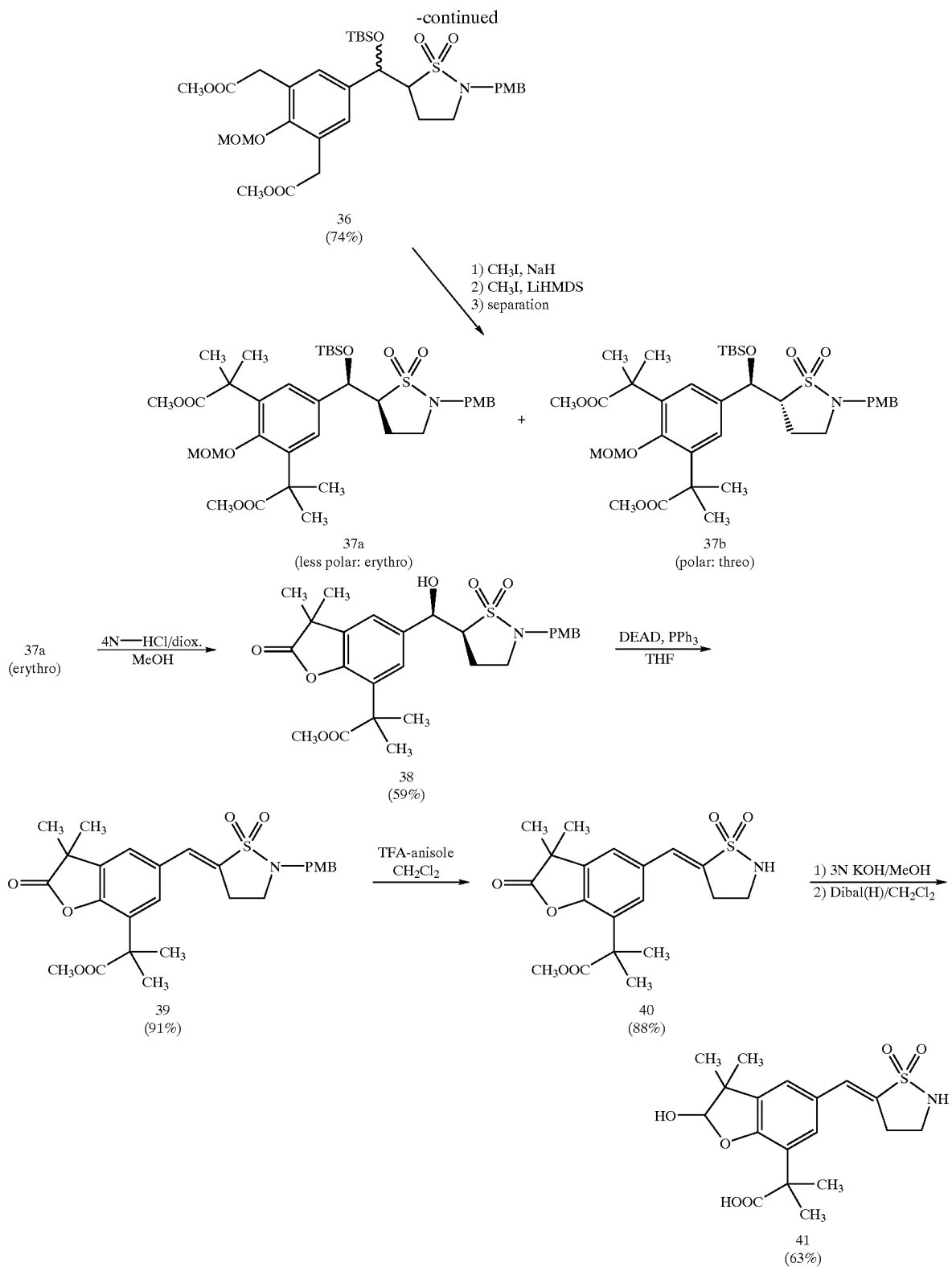

a. Compound 38

Using N-(4-methoxybenzyl)-1,2-isothiazolin-1,1-dioxide, 38 was prepared according to the synthesis of 28.

b. Methyl 2-(5-(2-(4-methoxy-benzyl)-1,1-dioxo-1,2-isothazolidin-5-ylidenemethyl)-3,3-dimethyl-2-oxo-2,3-dihydro-benzofuran-7-yl)-2-methyl-propionate (39)

To a solution of 38 (125 mg, 0.235 mmol) and Ph$_3$P (123 mg, 0.47 mmol) in THF (3 ml), DEAD (0.056 ml, 0.353 mmol) was slowly added under ice-cooling. After stirring for 1 hour, the reaction mixture was concentrated, and the residue was purified by silica gel chromatography to yield 110 mg (92%) of 39. $^1$H NMR (CDCl$_3$) δ: 1.26 (3H, t, J=7.2

Hz), 1.50 (6H, s), 1.61 (6H, s), 3.02–3.18 (4H, m), 3.71 (3H, s), 3.81 (3H, s), 4.18 (2H, s), 6.87–6.90 (2H, m), 7.14 (1H, d, J=1.8 Hz), 7.26–7.33 (4H, m).

c. 2-(5-(1,1-Dioxo-1,2-isothiazolidin-5-ylidenemethyl)-2-hydroxy-3,3-dimethyl-2,3-dihydro-benzofuran-7-yl)-2-methyl-propionic Acid (41)

To a solution of 39 (63 mg, 0.160 mmol) in methanol (4 ml), 3N KOH (2 ml) was added and the mixture was allowed to stand overnight at room temperature. The reaction mixture was concentrated, acidified with diluted hydrochloric acid, and extracted with ethyl acetate. The organic layer was washed with saturated brine, dried, and the solvent was removed in vacuo. The residue was added with dichloromethane (2 ml), cooled to −78° C., and dropwise and slowly added with DIBAL (0.93 M in n-hexane) (0.85 ml, 0.79 mmol). After 5 minutes, the mixture was added with diluted hydrochloric acid to quench the reaction and extracted with ethyl acetate. The organic layer was washed with saturated brine, dried, and concentrated. The residue was purified by preparative TLC to give 38 mg (63%) of 41. $^1$H NMR (d6-aceton) δ: 1.29 (6H, br), 1.57 (6H, s), 3.24 (2H, td, J=6.7, 2.5 Hz), 3.46 (2H, t, J=7.1 Hz), 5.67 (1H, s), 5.88 (12H, t, 53 (1H, br), 7.13 (1H, t, J=2.5 Hz), 7.32 (1H, 7.38 (1H, d, J=1.5 Hz), 10.7 (1H, br).

Example 4

Synthesis of 51 and 52

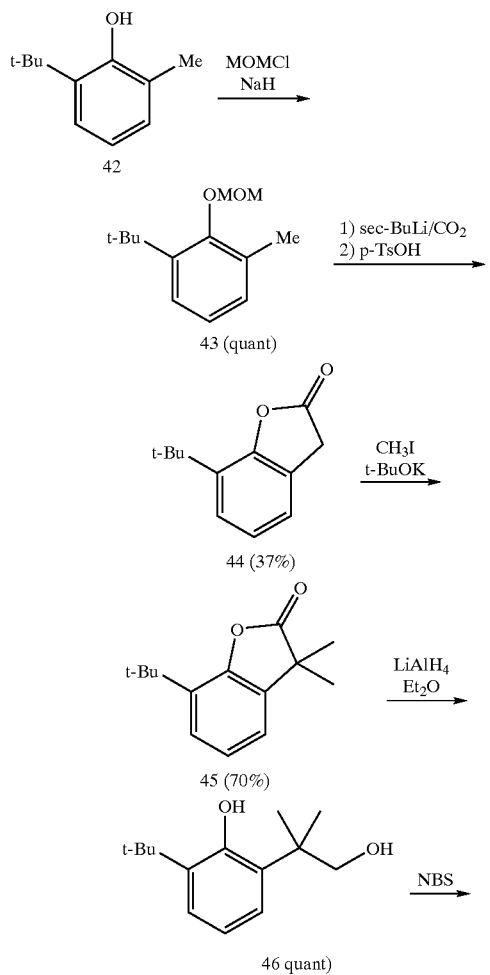

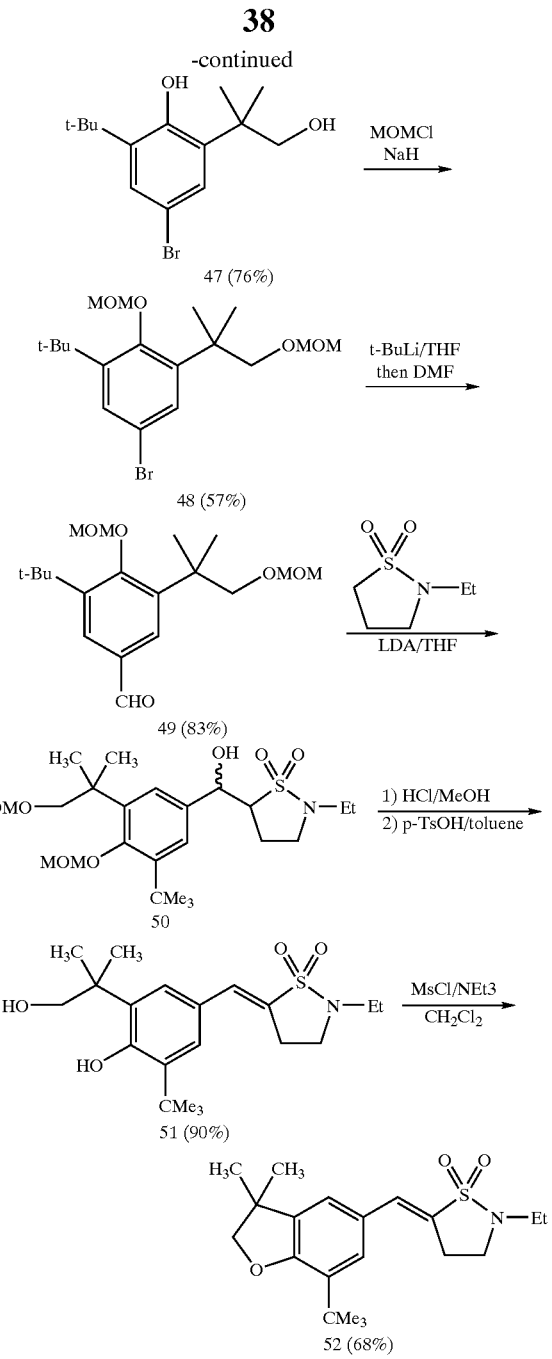

a. 3-tert-Butyl-2-methoxymethoxy-toluene (43)

NaH (60% in mineral oil, 4.5 g, 0.12 mol) is washed twice with hexane (50 ml) and added with THF (75 ml), and the mixture was cooled to below 10° C. A solution of 2-tert-butyl-6-methylphenol 42 (16.4 g, 0.1 mol) in THF (60 ml) was then dropwise and slowly added, and the mixture was stirred for 10 minutes under the same conditions. The mixture was then dropwise added with MOMCl (9.1 ml, 0.12 mol), warmed to room temperature, and the reaction mixture was added with saturated aqueous ammonium chloride (200 ml) and ethyl acetate (200 ml). The organic layer was separated, washed sequentially with water (200 ml), 1.5N NaOH (200 ml), water (100 ml), and saturated brine (200 ml), and dried. The solvent was removed in vacuo to give 20.5 g (98.6%) of 43 as colorless oil.

b. 7-tert-Butyl-2(3H)-benzofuranone (44)

A solution of 43 (3.0 g, 14.4 mmol) and TMEDA (2.6 ml, 17.3 mmol) in THF (40 ml) was cooled to −50° C., and dropwise and slowly added with sec-BuLi (1.3 M in cyclohexane, 13.3 ml, 17.3 mmol). The reaction mixture was warmed to −30° C., and then cooled again to −60° C., and dry ice was added to the mixture. The reaction mixture was warmed to room temperature over 1 hour, added with waster (50 ml) and ethyl acetate (50 ml). The aqueous layer was separated, acidified with 2N HCl to pH 3–4, and extracted with ethyl acetate (100 ml). The organic layer was washed with water (50 ml) and saturated brine (50 ml), and dried. The solvent was removed in vacuo. The residue was dissolved in toluene (50 ml), added with p-TsOH.H$_2$O (250 mg), and heated to reflux for 15 minutes. The reaction mixture was cooled to room temperature and poured into an aqueous diluted sodium bicarbonate solution (60 ml). The organic layer was separated and washed with saturated brine (60 ml). After drying, the solvent was removed in vacuo, and the residue was purified by column chromatography to yield 1.02 g (37%) of 44. $^1$H NMR (CDCl$_3$) δ: 1.40 (9H, s, tBu), 3.71 (2H, s, CH$_2$), 7.02–7.27 (3H, m, 3×Ar—H).

c. 7-tert-Butyl-3,3-dimethyl-2(3H)-benzofuranone (45)

A solution of 44 (300 mg, 1.577 mmol), CH$_3$I (0.29 ml, 4.73 mmol) and 18-Crown-6 (104 mg, 0.39 mmol) in THF (20 ml) was cooled to −50° C., and t-BuOK (389 mg, 3.47 mmol) was slowly added, and the mixture was stirred for 1 hour. The mixture was warmed to room temperature and stirred for another 1 hour. The reaction mixture was added with saturated aqueous ammonium chloride (30 ml) and extracted with ethyl acetate (30 ml). The organic layer was washed with water (30 ml), and saturated brine (30 ml), and dried. The solvent was removed in vacuo, and the residue was purified by column chromatography to yield 241 mg (70%) of 45. $^1$H NMR (CDCl$_3$) δ: 1.41 (9H, s, tBu), 1.50 (6H, s, 2×CH$_3$), 7.03–7.26 (3H, m, 3×Ar—H).

d. 2-tert-Butyl-6-(2-hydroxy-1,1-dimethylethyl)phenol (46)

A solution of 45 (235 mg, 1.077 mmol) in ether (5 ml) was dropwise added, with stirring and ice-cooling, to a suspension of LiAlH$_4$ (49 mg, 1.29 mmol) in ether (5 ml). After washing a container of the solution with ether (5 ml), the washing was added to the mixture, which was warmed to room temperature and stirred for 45 minutes. The reaction mixture was added with ethyl acetate (1 ml) and 3 ml of a mixture of water and saturated ammonium chloride (1:1), and stirred for 30 minutes. Resultant slurry was removed by filtration through celite, and the filtrate was concentrated to obtain 253 mg (quant) of 46. $^1$H NMR (CDCl$_3$) δ: 1.42 (9H, s, tBu), 1.44 (6H, s, 2×CH$_3$), 3.81 (2H, s, CH$_2$), 6.75–7.23 (3H, m, 3×Ar—H), 9.20 (1H, br s, phonemic-OH).

e. 4-Bromo-2-tert-butyl-6-(2-hydroxy-1,1-dimethylethyl)phenol (47)

To a solution of 46 (1.297 g, 5.83 mmol) in dichloromethane (20 ml), Py.HBr$_3$ (1.86 g, 5.83 mmol) was added all at once, with stirring and ice-cooling, and the mixture was stirred for 30 minutes. Water (30 ml) was added to the reaction mixture. The organic layer was separated and washed with water (30 ml). After drying, the solvent was removed in vacuo, and the residue was purified by column chromatography to yield 1.346 g (76%) of 47. $^1$H NMR (CDCl$_3$) δ: 1.39 (9H, s, tBu), 1.41 (6H, s, 2×CH$_3$), 3.79 (2H, s, CH$_2$), 7.20 (1H, d, J=2.4 Hz, Ar—H), 7.27 (1H, d, J=2.4 Hz, Ar—H), 9.45 (1H, br s, phonemic-OH).

f. 4-Bromo-2-tert-butyl-6-(2-methoxymethoxy-1,1-dimetylethyl)phenyl methoxymethyl Ether (48)

48 (930 mg, 56.9%) was prepared from 47 (1.264 g, 4.20 mmol), MOMCl (0.96 ml, 12.6 mmol) and NaH (402 mg, 10.5 mmol). $^1$H NMR (CDCl$_3$) δ: 1.41 (9H, s, tBu), 1.42 (6H, s, 2×CH$_3$), 3.31, 3.63 (each 3H, s, CH$_3$), 3.79 (2H, s, CH$_2$), 4.59, 4.89 (each 2H, s, CH$_2$), 7.36 (1H, d, J=2.8 Hz, Ar—H), 7.38 (1H, d, J=2.8 Hz, Ar—H)

g. 3-tert-Butyl-4-methoxymethoxy-5-(2-methoxymethoxy-1,1-dimethylethyl)benzaldehyde (49)

A solution of 48 (925 mg, 2.38 mmol) in THF (20 ml) was cooled to −50° C., and t-BuLi (1.7 M in pentane, 3.08 ml, 5.24 mmol) was dropwise added to the solution while maintaining the temperature below −40° C. After completion of the addition, the mixture was stirred at this temperature, and DMF (0.12 ml) in THF (5 ml) was added. The mixture was warmed slowly to room temperature. Aqueous solution of saturated ammonium chloride (50 ml) was added, and the mixture was extracted with ethyl acetate (50 ml). The organic layer was washed with saturated brine (50 ml), and after dryness, the solvent was removed in vacuo. The residue was purified by column chromatography to yield 669 mg (83.1%) of 49 as colorless oil. $^1$H NMR (CDCl$_3$) δ: 1.47 (9H, s, tBu), 1.48 (6H, s, 2×CH$_3$), 3.29, 3.66 (each 3H, s, CH$_3$), 3.84 (2H, s, CH$_2$), 4.60, 4.95 (each 2H, s, CH$_2$), 7.81 (1H, d, J=2.2 Hz, Ar—H), 7.84 (1H, d, J=2.2 Hz, Ar—H), 9.92 (1H, s, CHO).

h. (E)-2-Ethyl-5-[3-tert-butyl-4-hydroxy-5-(2-hydroxy-1,1-dimethylethyl)benzylidene]-1,2-isothiazolidie-1,1-dioxide (51)

Aldol adduct 50 (868 mg, 91.3%) was obtained as colorless oil from 49 (660 mg, 1.95 mmol) and N-Ethyl-1,2-isothiazolidine-1,1-dioxide (305.5 mg, 2.05 mmol). To a solution of this adduct 50 (790 mg, 1.62 mmol) in methanol (6 ml), about 10N HCl/MeOH (2 ml) was added, and the mixture was stirred at room temperature for 30 minutes and at 50° C. for 30 minutes. The reaction mixture was cooled to room temperature, and aqueous saturated sodium bicarbonate (50 ml) was added. The mixture was extracted with ethyl acetate (50 ml), and the organic layer was washed with saturated brine. After dryness, the solvent was removed in vacuo. Resultant residue-was dissolved in toluene (35 ml). p-TsOH.H$_2$O (50 mg) was added, and the mixture was heated to reflux for 10 minutes. The reaction mixture was cooled to room temperature, adsorbed to a small amount of silica gel, which was eluted with ethyl acetate (150 ml). The solvent was removed in vacuo, and the resultant residue was purified by column chromatography to yield 556 mg (90%) of 51 as colorless crystal. M.p. 152–155° C. IR (KBr) cm$^{-1}$: 3411, 3140, 2965, 1642, 1594, 1436, 1291, 1266, 1143.

$^1$H NMR (CDCl$_3$) δ: 1.28 (3H, t, J=7.2 Hz, CH$_3$), 1.41 (9H, s, tBu), 1.43 (6H, s, 2×CH$_3$), 2.95 (1H, t, J=3.8 Hz, alcoholic-OH), 3.07–3.33 (6H, m, 2×CH$_2$, CH$_2$), 3.81 (2H, d, J=3.8 Hz, CH$_2$), 7.17 (1H, d, J=2.0 Hz, Ar—H), 7.23 (1H, t, J=2.0 Hz, vinyl-H), 7.28 (1H, d, J=2.8 Hz, Ar—H), 9.92 (1H, s, phenolic-OH). Elementary analysis for C$_{20}$H$_{31}$NO$_4$S: Calcd: C, 62.96; H, 8.19; N, 3.67; S, 8.40. Found: C, 62.86; H, 8.19; N, 3.70; S, 8.30.

i. (E)-5-(7-tert-Butyl-3,3-dimethyl-2,3-dihydrobenzofuran-5-ylmethylene)-2-ethyl-1,2-isothiazolidine-1,1-dioxide (52)

A mixture of 51 (125 mg, 0.328 mmol), MsCl (30 μl, 0.394 mmol), triethylamine (114 μl, 0.82 mmol) and dichloromethane (10 ml) was stirred for 30 minutes under ice-cooling. The mixture was added with saturated brine (30 ml) and extracted with dichloromethane (30 ml). The organic layer was separated, and after dryness, the solvent was removed in vacuo. The residue was purified by column chromatography to yield 81 mg (68.1%) of 52. M.p. 104–106° C. IR (KBr) cm$^{-1}$: 3436, 2963, 2871, 1642, 1602, 1453, 1288, 1151. $^1$H NMR (CDCl$_3$) δ: 1.29 (3H, t, J=7.2 Hz, CH$_3$), 1.33 (6H, s, 2×CH$_3$), 1.35 (9H, s, tBu), 3.06–3.33

(6H, m, 2×CH$_2$, CH$_2$), 4.28 (2H, s, CH$_2$), 7.01 (1H, d, J=1.6 Hz, Ar—H), 7.15 (1H, d, J=1.6 Hz, Ar—H), 7.25 (1H, t, J=2.4 Hz, vinyl-H). Elementary analysis for C$_{20}$H$_{29}$NO$_3$S: calcd: C, 66.08; H, 8.04; N, 3.85; S, 8.82. Found: C, 66.14; H, 8.07; N, 3.82; S, 8.74.

The compound of the invention of formula Ia, as prepared in the above Preparation 15, was evaluated in vivo experiments for its usefulness as an antirheumatic agent, as an osteoclast formation inhibiting agent, as a nitrogen monoxide production inhibiting agent, and as a transcription factor NFκB suppressing agent.

Example 5

Antirheumatic Effect

1. Inhibitory Activity Against the Production of Cytokines

Cytokines are associated with production of proteases, collagenases, adhesion factors and the like, which are responsible for articular tissue destruction. Therefore, such articular tissue destruction could be suppressed by inhibition of cytokine production. One of these cytokines, IL-6, was used to evaluate the inhibitory activity of Compound Ia against the production of cytokine in the following manner.

Method

A neutrophil fraction from human peripheral blood was prepared, and 10 µg/mL of LPS (lipopolysaccharide) and Compound Ia were added to the fraction, and the mixture was then incubated for 16–18 hours. IL-6 was measured by RIA (radio immuno assay).

Result

Compound Ia inhibited the IL-6 production from neutrophil (IC$_{50}$: 20 µM) and inhibited the IL-6 production from synovial membrane cells of RA (rheumatic arthritis) patients (IC$_{50}$: 10 µM). Either of these inhibitory activities was greater than Tenidap, a comparative drug (Table 1).

TABLE 1

Inhibitory Activity Against IL-6 Production

| | IC$_{50}$ (µM) | |
|---|---|---|
| compound | neutrophil | synovial membrane cells from RA patient |
| Compound Ia | 20 | 10 |
| Tenidap | 50 | >50 |
| Indomethacin | nd | >50 | nd: not determined

2. Inhibitory Effect Against Rat Adjuvant Arthritis

A rat adjuvant arthritis model, which is commonly used in an in vivo evaluation for antirheumatic agents, was employed in this evaluation. To prepare an arthritis model, heat-killed cells of *Mycobacterium butyricum* (Difco) were suspended in mineral oil, and a rat was intradermally injected with 0.05 mL of 1% solution of the suspension at the plantar of left hind leg.

(i) Inhibitory Effect Against Articular Swelling

Method

Using the above arthritis model, Compound Ia was administered to the animal for 22 days after injection of the adjuvant, and the articular swelling was measured from time to time to evaluate the prophylactic inhibitory effect. On the other hand, the curative effect was evaluated by administering Compound Ia to animals from Day 15 to Day 25 after injection of the adjuvant and measuring the articular swelling in injected and non-injected legs. Inhibitory and curative effects were expressed by effective dose for 30% inhibition (ED$_{30}$).

Result

The results are graphically shown in FIG. 1 which shows the change in volume of the adjuvant-injected or non-injected leg. Compound Ia inhibited the articular swelling both in the adjuvant-injected and non-injected legs, and dose-dependent and significant inhibitory effect was observed particularly in the adjuvant-injected leg at a dose of 0.3 mg/kg/day or more. On the other hand, as for the curative effect, dose-dependent and significant inhibitory effect was observed at a dose of 3 mg/kg/day or more.

ED$_{30}$ values for prophylactic and curative effects of Compound Ia and the comparative drugs are shown in Table 2 below.

TABLE 2

Inhibitory Effect Against Adjuvant Articular Swelling

| | ED$_{30}$ (mg/kg/day) (95% confidence limits) | |
|---|---|---|
| compound | prophylactic effect | curative effect |
| Compound Ia | 0.88 (0.52–1.31) | 2.6 (1.3–6.4) |
| Tenidap | 0.98 (0.52–1.56) | 4.9 (2.4–23.0) |
| Cyclosporin A | 2.40 (1.90–3.00) | 4.7 (1.9–7.6) |
| Bucillamine | >50 | >50 |

(ii) Inhibitory Effect Against Articular Destruction

Method

Figure 2:
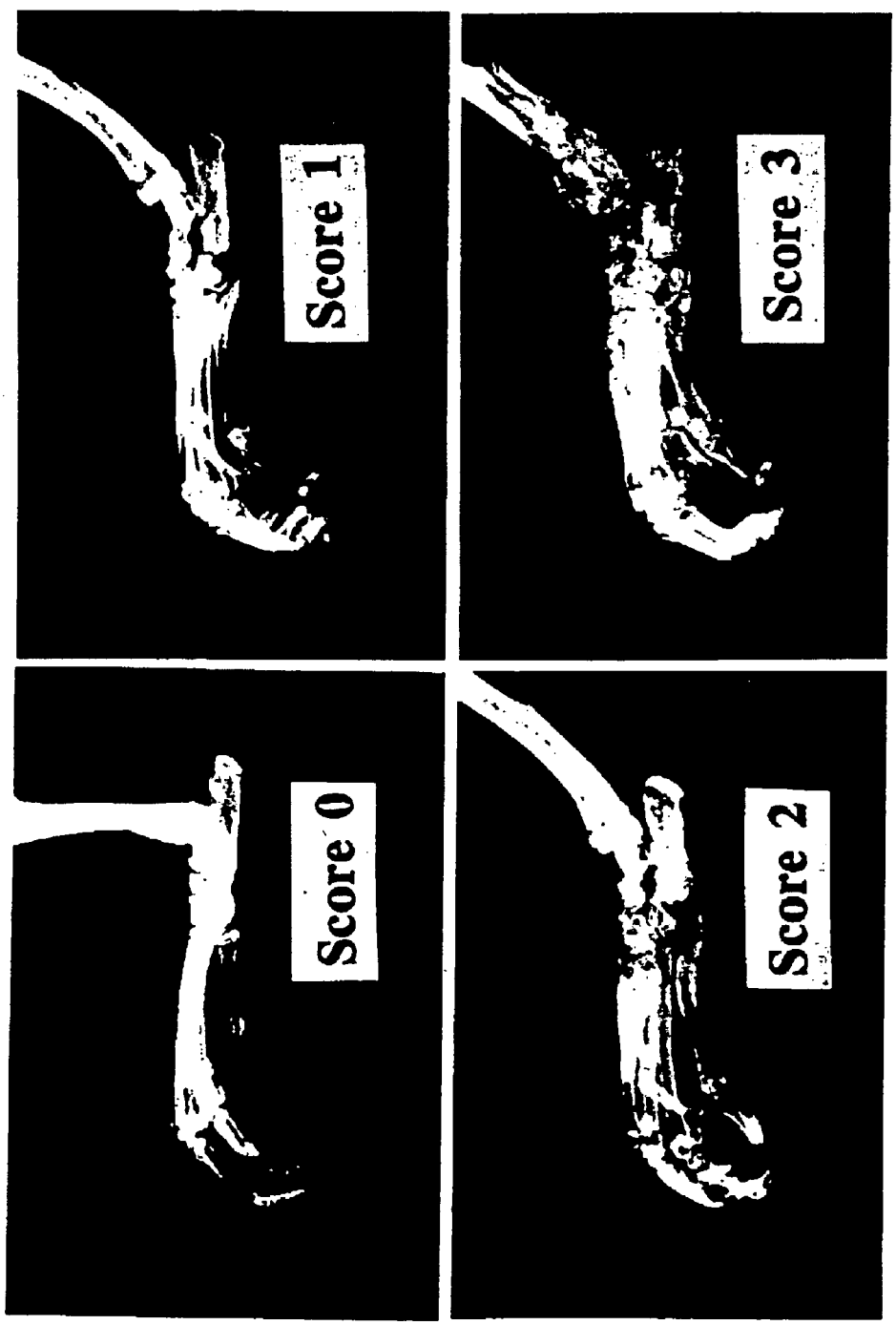
FIG. 2 is a X-ray observation score for bone destruction in arthrosis.

The right and left hind legs of the arthritis rats used in the above experiments were radiographed using a soft X-ray radiation and evaluated by the X-ray observation score for the bone destruction in the arthrosis. The effects were numerically evaluated by grading the articular destruction from 0 to 3 (0: normal; 1: low degree of articular and bone destruction; 2: medium degree of articular and bone destruction, and neogenesis of cartilage; 3: strong articular and bone destruction), and the efficacy in the drug-administered group was determined in comparison with the vehicle-administered group according to Wilcoxon U-test (*p<0.05, **p<0.01)(FIG. 2).

Result

Figure 3:
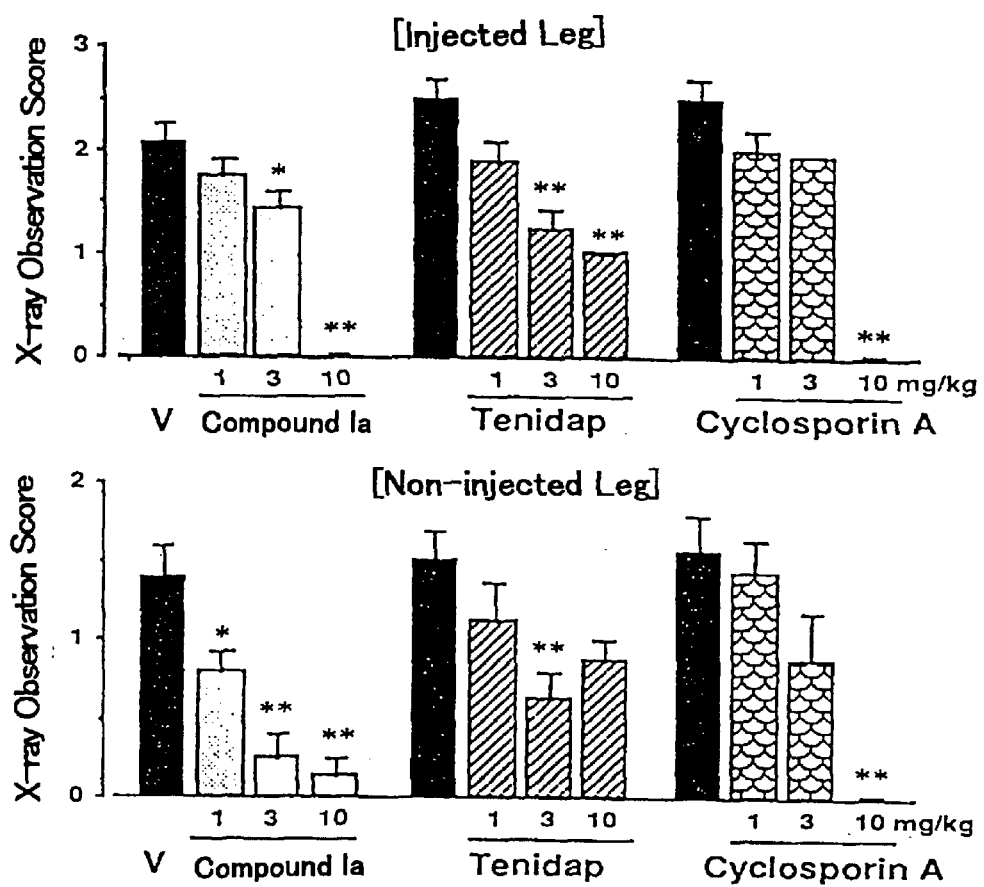
FIG. 3 is a graph showing the inhibitory effect against the destruction of articular bone in adjuvant arthritis. Values in the graph are mean±standard error of eight independent experiments, and significance test was performed according to Dunnett's t-test (*p<0.05, **p<0.01: vs. vehicle group).

Compound Ia exhibited dose-dependent and significant inhibitory effect against the articular destruction at a dose of 3 mg/kg/day or more in the adjuvant-injected leg and at a dose of 1 mg/kg/day or more in the non-injected leg. The inhibitory effect of the comparative drug, Tenidap, was comparable to that of Compound Ia in the adjuvant-injected leg, while the effect was lower than that of Compound Ia in the non-injected leg, although the drug exhibited significant inhibitory effect at a dose of 3 mg/kg/day. On the other hand, Cyclosporin A exhibited significant inhibitory effect at a dose of 10 mg/kg/day both in the adjuvant-injected and non-injected legs (FIG. 3).

(iii) Repressive Effect on the IL-6 Level in Articular Tissue

Method

Another adjuvant arthritis model animal was prepared apart from the above experiments, and a compound was orally administered to the animal for 18 days after the adjuvant injection. The non-injected leg was then amputated under anesthetization, epidermis of the amputated leg was ablated, the leg was frozen in liquid nitrogen, and the arthrosis part was crushed by a crushing machine. To a measured quantity of the crushed arthrosis, 3 mL of ice-cold PBS was added and homogenized with a homogenizer under ice-cooling. The resultant homogenate was centrifuged at 4° C. for 20 minutes at 3,000 rpm to collect the supernatant, which was then passed through a 0.45 µm filter to prepare a sample. The sample and MH60 BSF2 cells (derived from mouse, require IL-6) were incubated on a 96-well plate under defined conditions, and the absorbance was measured at two wave lengths of 540 nm and 690 nm. The IL-6 level in the sample was calculated based on the standard curve prepared using a recombinant human IL-6. The results were shown using mean±standard error of the data of seven animals, and significance test was performed according to Dunnett-t test (## $p<0.01$: vs. normal group; ** $p<0.01$: vs. vehicle group).

Result

Figure 4:
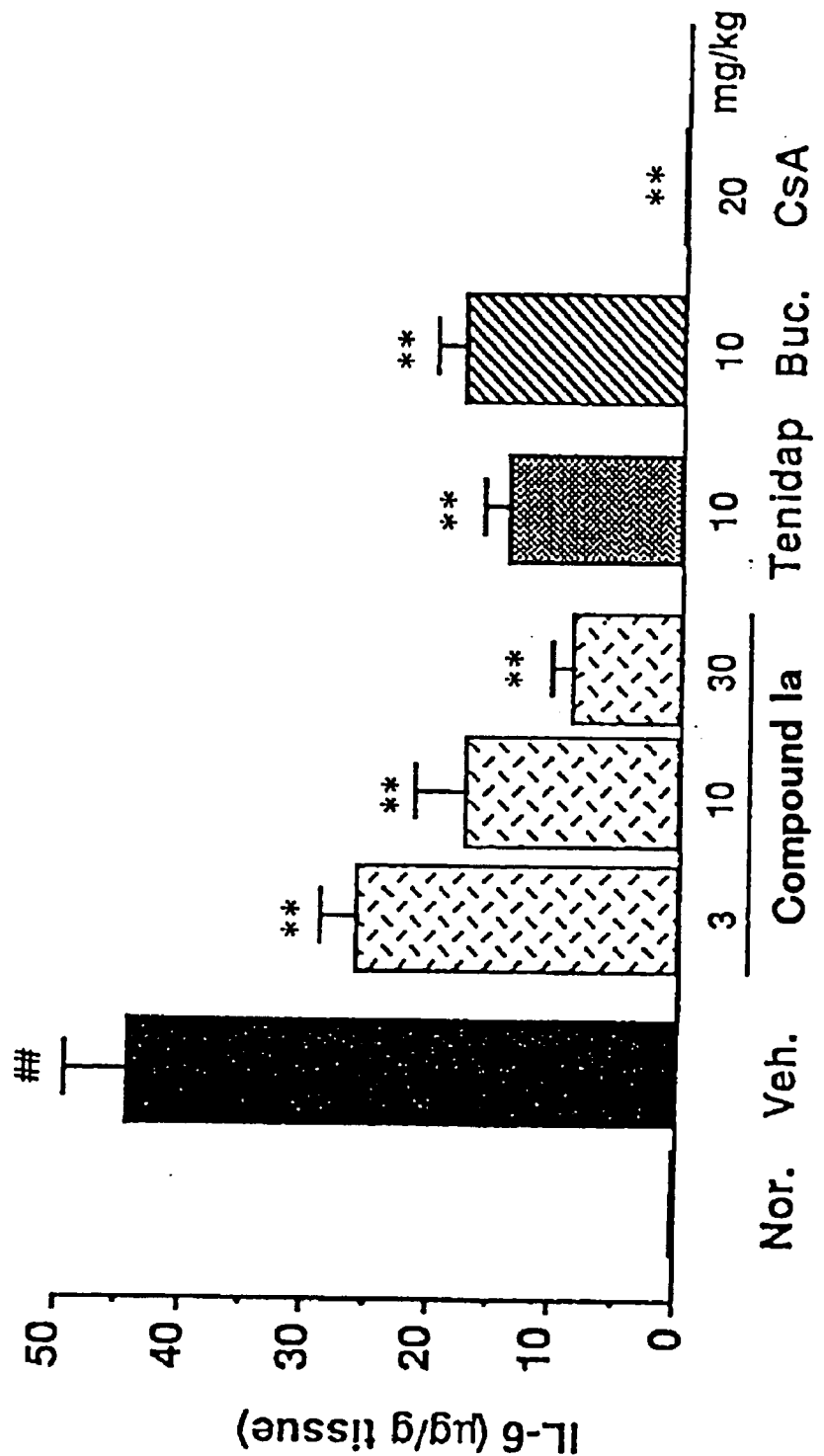
FIG. 4 is a graph showing the repressive effect on the IL-6 level in articular tissue. Nor: normal rat, Veh: vehicle, Buc: Bucillamine, CsA: Cyclosporin A. Values in the graph are mean±standard error of seven independent experiments, and significance test was performed according to Dunnett's t-test (##p<0.01: vs. normal group, **p<0.01: vs. vehicle group).

The IL-6 level in the articular tissue of the adjuvant arthritis rats (Veh.) was 44.2 μg/g tissue, indicating remarkable increase of IL-6 level compared to that of normal rats (Nor.). Compound Ia exhibited dose-dependent and significant inhibitory effect at a dose of 3 mg/kg/day or more against the increase of the IL-6 level in the articular tissue of pathologic animals. Tenidap and Bucillamine also exhibited significant inhibitory effect at a dose of 10 mg/kg/day, and their efficacies were comparable to that of Compound Ia. Cyclosporin A (CsA) at a dose of 20 mg/kg/day almost completely inhibited the increase of the IL-6 level (FIG. 4).

3. Inhibitory Effect Against Bone Destruction in Spontaneous Rheumatic Model Animal NZB/KN Mouse Method To male NZB/KN mice, in which a human RA-like pathology arises spontaneously due to their immunologically abnormal background, was orally administered Compound Ia once in a day (five times a week) for six months beginning at two-month-age. The mice which reached six month old (some were eight month old) were full-length radiographed under anesthetization and predetermined conditions using a soft X-ray generator (OM-55, Omic). According to the method of Nakamura, et. al. [*Arthritis. Rheum.*, 34, 171–179 (1991)], the number of the lesions observed in the bones and articular regions in the whole body were counted on the basis of the soft X-ray radiographed films, and the total number of the observed lesions were defined as the number of the bone disorders in the animal. The results were shown using mean±standard deviation, and significance test was performed according to Dunnett-t test (*$p<0.05$, ** $p<0.01$: vs. vehicle group).

Result

Figure 5:
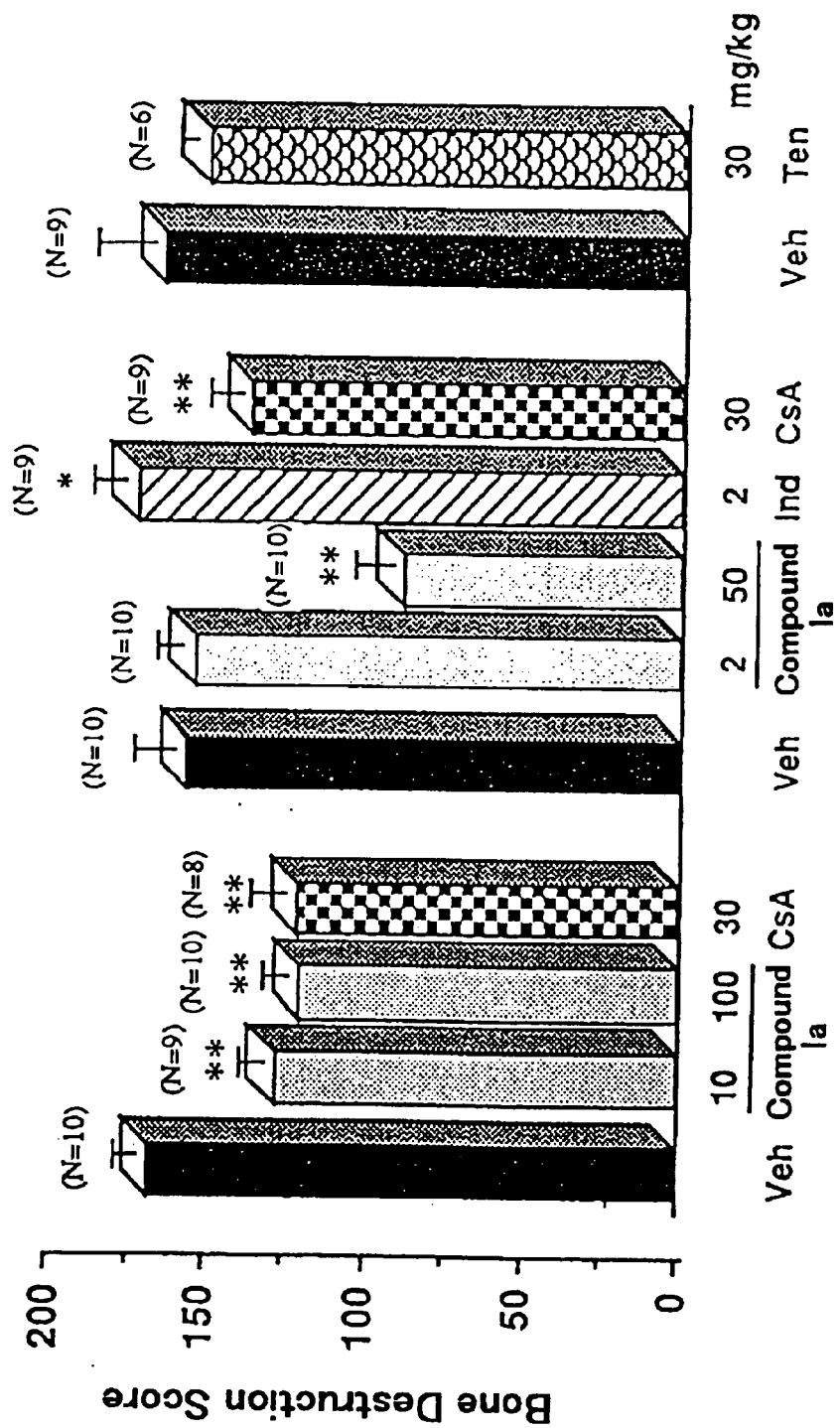
FIG. 5 is a graph showing the inhibitory effect against bone destruction in NZB/KN mouse. Veh: vehicle, CsA: Cyclosporin A, Ind: Indomethacin, Ten: Tenidap. N refers to the number of animals tested. Values in the graph are mean±standard error, and significance test was performed according to Dunnett's t-test (*p<0.05, **p<0.01: vs. vehicle group).

Compound Ia exhibited significant improving effect on the bone-articular lesions at a dose of 10 mg/kg/day or more. As for the comparative drugs, Tenidap (Ten) and Cyclosporin A (CsA), which were each administered at a dose of 30 mg/kg/day, Cyclosporin A exhibited significant inhibitory effect while Tenidap was not effective. On the other hand, Indomethacin at a dose of 2 mg/kg/day exhibited no inhibitory effect but significant enhancing effect on the bone destruction (FIG. 5).

4. Effect on MRL/l Mouse Blood Acute Phase Protein (Serum Amyloid Protein: SAP)

Method

To MRL/l male mice known as a lupus mouse in which a human RA-like pathology spontaneously arises, Compound Ia was orally administered five times a week (twice a week for Predonisolone) for 13 weeks. After the last administration of the compound, blood was collected under anesthetization, and the serum was used for SAP measurement. SAP has been used as a marker for rheumatism. A 96-well plate was coated with rabbit anti-mouse SAP serum, and the serum to be tested was then added to the plate and incubated for 2 hours. After addition of sheep anti-mouse SAP serum, a rabbit anti-sheep IgG antibody labeled with alkaline phosphatase and then a substrate were added to the plate, and OD of developed color was measured at 405 nm. The results were shown using mean±standard error, and significance test of the results was performed according to Dunnett-t test (*$p<0.05$, **$p<0.01$: vs. vehicle group).

Result

Figure 6:
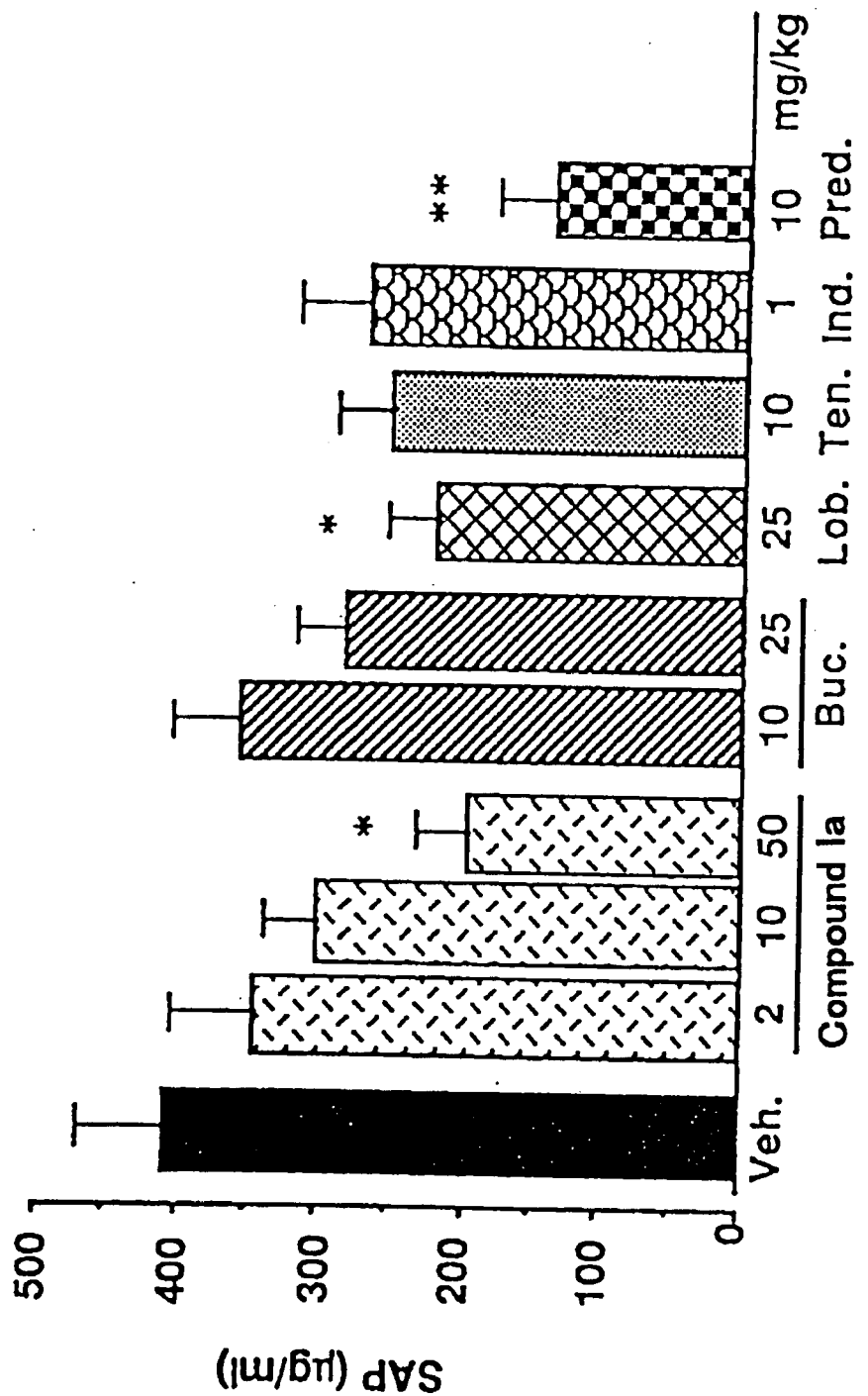
FIG. 6 is a graph showing the repressive effect on MRL/l mouse blood acute phase protein SAP. Veh: vehicle, Buc: Bucillamine, Lob: Lobenzarit, Ten: Tenidap, Ind: Indomethacin, and Pred: Predonisolone. Values in the graph are mean±standard error, and significance test was performed according to Dunnett's t-test (*p<0.05, **p<0.01: vs. vehicle group).

The groups which received Compound Ia at a dose of 2–50 mg/kg/day exhibited repressive tendency in a dose-dependent manner, and the dose of 50 mg/kg/day gave significant results. Significant inhibitory effects were also observed in the groups which received comparative drugs, Lobenzarit (Lob.) at a dose of 25 mg/kg/day and Predonisolone (Pred.) at a dose of 10 mg/kg/day. However, the groups which received Tenidap (Ten.) at a dose of 10 mg/kg/day, Indomethacin (Ind.) at a dose of 1 mg/kg/day and Bucillamine (Buc.) at a dose of 10 or 25 mg/kg/day gave no significant results although they exhibited suppressive tendency (FIG. 6).

Example 6

Inhibitory Effect Against Osteoclast Formation

Inhibitory Effect Against Enhanced Formation of Osteoclast in Mouse Myeloblast

Method

It has been known that the enhanced formation of osteoclast is induced in the mouse myeloblast culture by addition of IL-1β and such effect is derived from $PGE_2$ production through COX-2 induction. In order to determine inhibitory effect of the compounds against such effect, myeloblasts were collected from a ddY male mice, plated in a 48-well plate at $1\times10^6$/well and incubated. After culturing for six days in an α-MEM medium containing 10% fetal bovine serum, to which 2.5 ng/mL of human IL-1β and a predetermined concentration of the compounds were added, $PGE_2$ level in the supernatant was measured by RIA kit. On the other hand, cells adhering on the plate were immobilized, and an activity staining of tartaric acid resistant acid phosphatase (TRAP), which is a marker enzyme for osteoclast, was conducted, whereby the number of TRAP positive cells having multinucleate (N>3) per well was counted as osteoclast.

Result

Test compounds were added to the above culture and assayed for their inhibitory activity against the $PGE_2$ production due to IL-1β stimulation and the enhanced formation of osteoclast. The results were shown in terms of $IC_{50}$ (Table 3). Compound Ia exhibited stronger inhibition as compared with Tenidap and Indomethacin. The inhibition of Compound Ia was greater than that of N-[2-(cyclohexyloxy)-4-nitrophenyl]-methanesulfoneamide, a selective COX-2 inhibitor.

TABLE 3

Inhibitory Activity Against Enhanced Formation of Osteoclast and $PGE_2$ Production

| | $IC_{50}$ (μM) | |
|---|---|---|
| compound | Inhibition of Osteoclast Formation | Inhibition of $PGE_2$ Production |
| Compound Ia | 0.0013 | 0.00021 |
| Tenidap | 0.063 | 0.0017 |
| Indomethacin | 0.032 | 0.0064 |
| N-[2-(cyclohexyloxy)nitrophenyl]methanesulfoneamide | 0.024 | 0.0042 |

Example 7

Inhibitory Effect Against Nitrogen Monoxide Production

1. Inhibitory Activity Against NO Production from Activated Macrophage (MΦ)

Method

To BALB/c male mice was intraperitoneally administered 2 mL of a thioglycolate solution, and induced activated MΦ were collected after four days and used as NO producing cells. The cells were adjusted to $2\times10^6$ cells/mL and plated onto a 96-well microtiter plate at $2\times10^5$ cells/100 µL/well. 10 µL of 1 µg/mL of Compound Ia and LPS (lipopolysaccharide) were added thereto and incubated at 37° C. under 5% $CO_2$ for 24 hours. 75 µL of the supernatant obtained after incubation and 75 µL of Griess reagent were incubated, and $NO^{2-}0$ in the form of sodium nitrite was measured to determine the amount of NO in the supernatant.
Result Compound Ia at 0.8–12.5 µM inhibited NO production in a dose-dependent manner in the above assay system. The inhibitory activity of Compound Ia against NO production was greater than those of the comparative agents, Tenidap and Indomethacin (Table 4).

Figure 7:
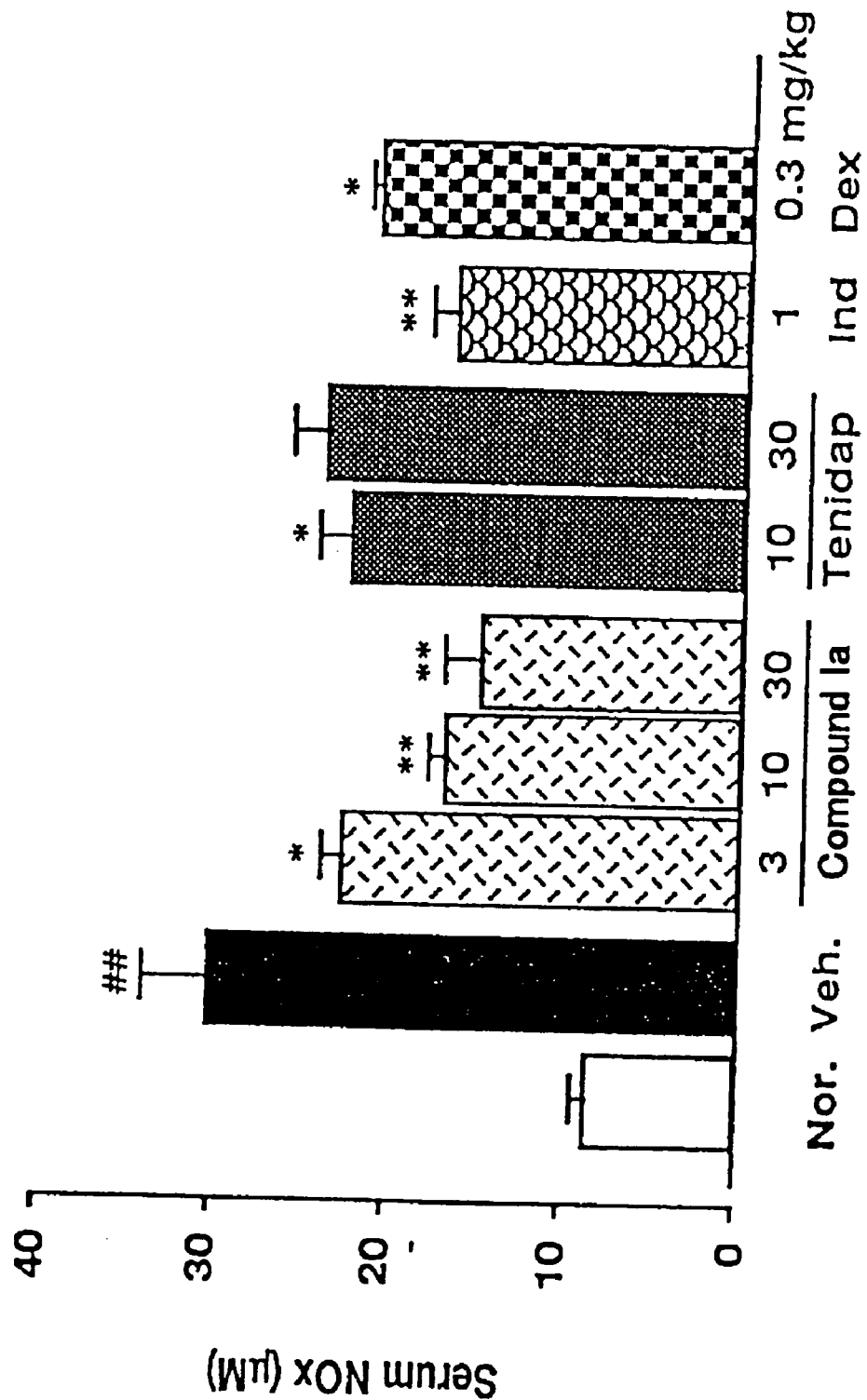
FIG. 7 is a graph showing the repressive effect on suppressive effect on blood NOx level in adjuvant arthritis rat. Nor: normal rat, Veh: vehicle, Ind: Indomethacin, and Dex: Dexamethazon. Values in the graph are mean±standard error of eight independent experiments, and significance test was performed according to Dunnett's t-test (##p<0.01: vs. normal group, *p<0.05, **p<0.01: vs. vehicle group).

Ia at a dose of 3 mg/kg/day or more exhibited the dose-dependent and significant inhibitory effect on the increase of blood NOx level in this pathological animal. As for the comparative drug, Tenidap, significant effect was observed at 10 mg/kg/day, while mere inhibitory tendency was observed at 30 mg/kg/day. Thus, the inhibitory effect of Tenidap was lower than that of Compound Ia. Indomethacin (Ind) at 1 mg/kg/day and Dexamethazon (Dex) at 0.3 mg/kg/day also exhibited significant inhibitory effect (FIG. 7).

Example 8
Suppressive Effect on Transcription Factor NFκB Suppressive Activity on Transcription Factor NFκB
Method A recombinant plasmid (pGV-B.HIV-1LTR), in which HIV-1 (AIDS) virus promoter LTR containing two NFκB

TABLE 4

Inhibitory Activity Against NO Production In Mouse Activated Macrophage
$NO^{2-}$ Production (µM/2 × $10^5$ cells)

| Medium | <0.1 | | |
|---|---|---|---|
| Medium + LPS | 28.3 ± 2.29 | | |
| µM | Compound Ia | Tenidap | Indomethacin |
| 0.8 | 27.3 ± 0.94 | 31.5 ± 1.05 | 29.5 ± 0.68 |
| 3.1 | 12.3 ± 2.50** | 33.1 ± 0.75 | 27.9 ± 1.91 |
| 12.5 | <1.0*** | 36.2 ± 0.91* | 23.9 ± 2.49 |
| 50 | <1.0*** | 19.7 ± 0.96** | 14.9 ± 3.02** |
| 100 | <1.0*** | 3.3 ± 1.99*** | 3.0 ± 2.41*** |
| $IC_{50}$ (µM) | 3.0 | 75.0 | 60.0 |

Values in the table are mean ± standard error of independent experiments. *p < 0.05, p < 0.01, *p < 0.001: Student t-test 2. Suppressive Effect on Blood NO Level
Method An adjuvant arthritis model was prepared in the same manner as above, and the compounds were orally administered to the animals for 28 days beginning on the day before the adjuvant injection. Blood was then collected under anesthetization and the serum was ultracentrifuged. The supernatant was ultrafiltrated to prepare a sample for NOx (nitrite+nitrate) measurement. Serum NOx level was determined by the measurement of optical density at 550 nm using the improved absorptiometry by Griess [Tracy, W. R. Tse, J., and Carter, G., (1995), J. Pharmacol. Exp. Ther., 272, 1011–1015]. The results were shown using mean±standard error of the data of eight samples, and significance test was performed according to Dunnett's t-test (##p<0.01: vs. normal group; *p<0.05, **p<0.01: vs. vehicle group).
Result Serum NOx level in the arthritis-maturing phase on 28th day after adjuvant administration was increased by about three times as compared with the normal level. Compound binding sites is ligated to upstream of firefly luciferase gene, was constructed, and the DNA was purified. This plasmid DNA was introduced by electroporation into a Jurkat cell, a human T cell leukemic cell line, and the cell was cultured for 48 hours. Subsequently, phytohemagglutinin (PHA, 0.5%), phorbol ester (TPA (12-O-tetradecanoylphorbol 13-acetate), 25 ng/mL), and a predetermined concentration of the test compound were added thereto to allow to react for 2 hours, and the cells were harvested, and the luciferase activity in the cellular extract was measured.
Result Compound Ia inhibited luciferase activity at 5–50 µM in a dose-dependent manner (Table 5, Experiment-1). The comparative drugs, Tenidap and Lobenzarit, inhibited the activity at 20–50 µM and at 500 µM, respectively, while their efficacies were lower than that of Compound Ia. No inhibitory effect was observed for Bucillamine even at 500 µM (Table 5, Experiment-1 and Experiment-2).

TABLE 5

Suppressive Activity on Transcription Factor NFκB

| | luciferase activity (%) | | | | luciferase activity (%) | | |
|---|---|---|---|---|---|---|---|
| Experiment-1 | µM | N | mean ± standard error | Experiment-2 | µM | N | mean ± standard error |
| control | | 2 | 26.9 ± 1.5 | control | | 2 | 44.1 ± 9.4 |
| TPA-PHA | | 4 | 100.0 ± 2.5 | TPA-PHA | | 2 | 100.0 ± 4.6 |
| Compound Ia | 5 | 4 | 82.2 ± 8.3 | Compound Ia | 20 | 2 | 86.4 ± 1.9 |
| | 10 | 4 | 79.6 ± 5.4 | | 50 | 1 | 75.1 |
| | 20 | 4 | 54.6 ± 4.3 | | 100 | 2 | 61.1 ± 3.9 |
| | 50 | 4 | 53.5 ± 5.9 | Lobenzarit | 20 | 2 | 112.6 ± 1.9 |

TABLE 5-continued

Suppressive Activity on Transcription Factor NFκB

| | luciferase activity (%) | | | | luciferase activity (%) | | |
|---|---|---|---|---|---|---|---|
| Experiment-1 | $\mu$M | N | mean ± standard error | Experiment-2 | $\mu$M | N | mean ± standard error |
| Tenidap | 5 | 4 | 94.0 ± 14.0 | | 100 | 2 | 100.6 ± 2.7 |
| | 10 | 4 | 94.4 ± 7.2 | | 500 | 2 | 70.6 ± 4.9 |
| | 20 | 3 | 75.6 ± 19.1 | Bucillamine | 20 | 1 | 96.0 |
| | 50 | 4 | 69.3 ± 17.1 | | 100 | 2 | 96.1 ± 6.2 |
| | | | | | 500 | 2 | 101.0 ± 0.8 |

Values in the table are mean ± standard error of independent experiments in terms of relative luciferase activity.

Values in the table are mean±standard error of independent experiments in terms of relative luciferase activity.

Example 9

| Formulations | |
|---|---|
| 1) Granules | |
| Compound of the invention | 20 mg |
| Lactose | 250 mg |
| Corn starch | 115 mg |
| Hydroxypropylcellulose | 115 mg |

Above materials are granulated in a conventional wet process to obtain granules.

EFFECT OF THE INVENTION

The compounds of the present invention have an inhibitory effect against articular bone destruction and the like in a rheumatic model animal, and yet the inhibitory effect against the production of IL-6 and acute phase proteins such as serum amyloid. Accordingly, the compounds of the invention are useful as an antirheumatic agent for prevention and/or treatment of rheumatoid arthritis.

Also, since the compounds of the present invention have an inhibitory effect against the enhanced formation of osteoclast in mouse myeloblasts, they are useful as an preventing and/or treating agent for bone metabolic disorders such as rheumatoid arthritis, osteoarthritis and osteoporosis and the like.

Further, the compounds of the present invention are useful for prevention and/or treatment of rheumatoid arthritis and osteoarthritis since they exhibit an inhibitory effect against NO production in macrophage which has received an inflammatory stimulus and NO production in an inflammatory pathological model animal. Due to inhibitory effect against NO production, the compounds of the invention would be useful for prevention and/or treatment of atherosclerosis, ischemic heart and brain disease, Alzheimer disease, diabetes, endotoxin shock, sepsis, ulcerative colitis and the like.

Furthermore, since the compounds of the invention exhibit a suppressive effect on NFκB in human cells, they are useful for prevention and/or treatment of chronic articular rheumatism. Based on the suppressive effect on NFκB, the compounds of the invention would also be useful for systemic lupus erythematosus, Behcet's disease, ulcerative colitis, atherosclerosis, endotoxin shock, sepsis, cytomegalovirus pneumonia, adenovirus cold, AIDS and the like.

What is claimed is:

1. A compound of formula I':

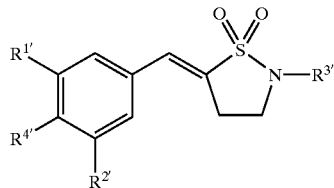

wherein
$R^{1'}$ is hydroxy lower alkyl or carboxy lower alkyl and $R^{4'}$ is hydroxy; or
$R^{1'}$ and $R^{4'}$ taken together form —$CR^5R^6$—$(CH_2)_m$—O— or —$CR^5R^6$—$(CH_2)_p$CH(OH)—O—
wherein m is an integer of 1 to 3;
p is an integer of 0 to 2; and
$R^5$ and $R^6$ are each independently hydrogen, lower alkyl, lower alkoxy, or hydroxy lower alkyl;
$R^{2'}$ is hydrogen, lower alkyl, lower alkoxy, hydroxy lower alkyl, or carboxy lower alkyl; and
$R^{3'}$ is hydrogen, lower alkyl, cycloalkyl, lower alkoxy, arylalkyloxy, heteroarylalkyloxy, lower alkylcarbonyl, arylcarbonyl, substituted or unsubstituted carbamoyl or a group represented by the formula:

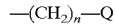—$(CH_2)_n$—Q wherein Q is hydroxy, substituted or unsubstituted amino, aryl, heteroaryl, hydroxycarbonyl or lower alkyloxycarbonyl; and
n is an integer of 0 to 3
or a pharmaceutically acceptable salt or hydrate thereof.

2. The compound of claim 1, wherein $R^{1'}$ is hydroxy lower alkyl or carboxy lower alkyl and $R^{4'}$ is hydroxy.

3. The compound of claim 1, wherein $R^{1'}$ and $R^{4'}$ taken together form —$CR^5R^6$—$(CH_2)_m$—O— or —$CR^5R^6$—$(CH_2)_p$CH(OH)—O—
wherein m is an integer of 1 to 3;
p is an integer of 0 to 2; and
$R^5$ and $R^6$ are each independently hydrogen, lower alkyl, lower alkoxy, or hydroxy lower alkyl.

4. The compound of claim 1, wherein $R^{1'}$ is 1,1-dimethyl-2-hydroxyethyl or 1,1-dimethyl-2-carboxyethyl and $R^{4'}$ is hydroxy.

5. The compound of claim 1, wherein $R^{1'}$ and $R^{4'}$ taken together form —$C(CH_3)_2$—$CH_2$—O— or —$C(CH_3)_2$—CH(OH)—O—.

* * * * *